(12) United States Patent
Amodeo et al.

(10) Patent No.: US 9,102,710 B2
(45) Date of Patent: Aug. 11, 2015

(54) CYCLIC PEPTIDES BINDING CXCR4 RECEPTOR AND RELATIVE MEDICAL AND DIAGNOSTIC USES

(75) Inventors: Pietro Amodeo, Pozzuoli (IT); Rosamaria Vitale, Pozzuoli (IT); Stefania De Luca, Naples (IT); Stefania Scala, Naples (IT); Giuseppe Castello, Naples (IT); Alfredo Siani, Naples (IT)

(73) Assignee: IRCCS-ISTITUTO NAZIONALE PER LO STUDIO E LA CURA DEI TUMORI "FONDAZIONE GIOVANNI PASCALE", Naples (IT)

(*) Notice: Subject to any disclaimer, the term of this patent is extended or adjusted under 35 U.S.C. 154(b) by 0 days.

(21) Appl. No.: 13/575,377

(22) PCT Filed: Jan. 20, 2011

(86) PCT No.: PCT/IB2011/000120
§ 371 (c)(1),
(2), (4) Date: Oct. 16, 2012

(87) PCT Pub. No.: WO2011/092575
PCT Pub. Date: Aug. 4, 2011

(65) Prior Publication Data
US 2013/0079292 A1    Mar. 28, 2013

(30) Foreign Application Priority Data
Jan. 26, 2010 (IT) .............................. MI2010A0093

(51) Int. Cl.
*C07K 7/64* (2006.01)
*C07K 7/06* (2006.01)
*A61K 38/00* (2006.01)

(52) U.S. Cl.
CPC ... *C07K 7/64* (2013.01); *C07K 7/06* (2013.01); *A61K 38/00* (2013.01)

(58) Field of Classification Search
CPC ............ H01L 21/2018; H01L 21/2257; H01L 29/0649; H01L 29/66287; H01L 29/732; A61K 38/00; C07K 7/06; C07K 7/64
See application file for complete search history.

(56) References Cited

U.S. PATENT DOCUMENTS

2010/0130409 A1    5/2010 Kohn

OTHER PUBLICATIONS

International Search Report Dated Jun. 8, 2008.

*Primary Examiner* — Thomas S Heard
(74) *Attorney, Agent, or Firm* — Hedman & Costigan, P.C.; James V. Costigan; Kathleen A. Costigan

(57) ABSTRACT

The present invention relates to the identification of new peptides and peptidomimetics which bind the CXCR4 receptor, capable of forming complexes with receptors for chemokines, in particular with CXCR4. The invention also relates to the use of these peptides for the treatment, prevention and diagnosis of diseases which involve chemokine receptors (i.e. neoplasias, metastases, HIV-1 virus infections), and also the mobilization of stem cells of hemopoietic precursors in the case of autologous transplants. Finally, the invention comprises pharmaceutical compositions and diagnostic kits comprising said peptides.

5 Claims, 5 Drawing Sheets

```
                        SEQUENCE LISTING

<160> NUMBER OF SEQ ID NOS: 24

<210> SEQ ID NO 1
<211> LENGTH: 5
<212> TYPE: PRT
<213> ORGANISM: Artificial sequence
<220> FEATURE:
<223> OTHER INFORMATION: Synthetic cyclic peptide
<220> FEATURE:
<221> NAME/KEY: DISULFID
<222> LOCATION: (1)..(5)
<223> OTHER INFORMATION: Disulfide bond between Ac-C and C-Nam
<220> FEATURE:
<221> NAME/KEY: ACETYLATION
<222> LOCATION: (1)..(1)
<223> OTHER INFORMATION: Acetyl-Cystein
<220> FEATURE:
<221> NAME/KEY: AMIDATION
<222> LOCATION: (5)..(5)
<223> OTHER INFORMATION: N Amidation of C-terminal Cys

<400> SEQUENCE: 1

Cys Trp His Arg Cys
1               5

<210> SEQ ID NO 2
<211> LENGTH: 5
<212> TYPE: PRT
<213> ORGANISM: Artificial sequence
<220> FEATURE:
<223> OTHER INFORMATION: Synthetic cyclic peptide
<220> FEATURE:
<221> NAME/KEY: DISULFID
<222> LOCATION: (1)..(5)
<223> OTHER INFORMATION: Disulfide bond between N terminal and
      C-terminal Cys

<400> SEQUENCE: 2

Cys Phe Phe Arg Cys
1               5

<210> SEQ ID NO 3
<211> LENGTH: 5
<212> TYPE: PRT
<213> ORGANISM: Artificial sequence
<220> FEATURE:
<223> OTHER INFORMATION: Synthetic cyclic peptide
<220> FEATURE:
```

```
<221> NAME/KEY: DISULFID
<222> LOCATION: (1)..(5)
<223> OTHER INFORMATION: Disulfide bond between N terminal and
      C-terminal Cys

<400> SEQUENCE: 3

Cys Trp His Arg Cys
1               5

<210> SEQ ID NO 4
<211> LENGTH: 7
<212> TYPE: PRT
<213> ORGANISM: Artificial sequence
<220> FEATURE:
<223> OTHER INFORMATION: Synthetic cyclic peptide
<220> FEATURE:
<221> NAME/KEY: DISULFID
<222> LOCATION: (3)..(7)
<223> OTHER INFORMATION: Disulfide bond between Cys in position 3 and
      C-terminal Cys

<400> SEQUENCE: 4

Arg Ala Cys Arg Tyr Trp Cys
1               5

<210> SEQ ID NO 5
<211> LENGTH: 5
<212> TYPE: PRT
<213> ORGANISM: Artificial sequence
<220> FEATURE:
<223> OTHER INFORMATION: Synthetic cyclic peptide
<220> FEATURE:
<221> NAME/KEY: DISULFID
<222> LOCATION: (1)..(5)
<223> OTHER INFORMATION: Disulfide bond between N-terminal and
      C-terminal Cys
<220> FEATURE:
<221> NAME/KEY: AMIDATION
<222> LOCATION: (5)..(5)
<223> OTHER INFORMATION: N Amidation of C-terminal Cys

<400> SEQUENCE: 5

Cys Phe Phe Arg Cys
1               5

<210> SEQ ID NO 6
<211> LENGTH: 7
<212> TYPE: PRT
<213> ORGANISM: Artificial sequence
<220> FEATURE:
<223> OTHER INFORMATION: Synthetic cyclic peptide
<220> FEATURE:
<221> NAME/KEY: DISULFID
<222> LOCATION: (1)..(5)
<223> OTHER INFORMATION: Disulfide bond between N terminal Cys and Cys
      in position 5

<400> SEQUENCE: 6

Cys Trp Tyr Arg Cys Ala Arg
1               5

<210> SEQ ID NO 7
<211> LENGTH: 7
<212> TYPE: PRT
<213> ORGANISM: Artificial sequence
<220> FEATURE:
<223> OTHER INFORMATION: Synthetic cyclic peptide
<220> FEATURE:
<221> NAME/KEY: DISULFID
<222> LOCATION: (3)..(7)
<223> OTHER INFORMATION: Disulfide bond between Cys in position 3 and C
``` terminal Cys

<400> SEQUENCE: 7

Arg Ala Cys Arg Phe Phe Cys
1               5

<210> SEQ ID NO 8
<211> LENGTH: 7
<212> TYPE: PRT
<213> ORGANISM: Artificial sequence
<220> FEATURE:
<223> OTHER INFORMATION: Synthetic cyclic peptide
<220> FEATURE:
<221> NAME/KEY: DISULFID
<222> LOCATION: (3)..(7)
<223> OTHER INFORMATION: Disulfide bond between the Cys in position 3
      and C-terminal Cys

<400> SEQUENCE: 8

Arg Ala Cys Arg His Trp Cys
1               5

<210> SEQ ID NO 9
<211> LENGTH: 5
<212> TYPE: PRT
<213> ORGANISM: Artificial sequence
<220> FEATURE:
<223> OTHER INFORMATION: Synthetic cyclic peptide
<220> FEATURE:
<221> NAME/KEY: BINDING
<222> LOCATION: (1)..(5)
<223> OTHER INFORMATION: Peptide bond (backbone-backbone) between N
      terminal B-Ala and C-terminal B-Ala
<220> FEATURE:
<221> NAME/KEY: MISC_FEATURE
<222> LOCATION: (1)..(1)
<223> OTHER INFORMATION: Beta-alanine
<220> FEATURE:
<221> NAME/KEY: MISC_FEATURE
<222> LOCATION: (5)..(5)
<223> OTHER INFORMATION: Beta alanine

<400> SEQUENCE: 9

Ala Trp His Arg Ala
1               5

<210> SEQ ID NO 10
<211> LENGTH: 7
<212> TYPE: PRT
<213> ORGANISM: Artificial sequence
<220> FEATURE:
<223> OTHER INFORMATION: Synthetic cyclic peptide
<220> FEATURE:
<221> NAME/KEY: DISULFID
<222> LOCATION: (1)..(5)
<223> OTHER INFORMATION: Disulfide bond between N-terminal Cys and Cys
      in position 5

<400> SEQUENCE: 10

Cys Trp His Arg Cys Ala Arg
1               5

<210> SEQ ID NO 11
<211> LENGTH: 5
<212> TYPE: PRT
<213> ORGANISM: Artificial sequence
<220> FEATURE:
<223> OTHER INFORMATION: Synthetic cyclic peptide
<220> FEATURE:
<221> NAME/KEY: DISULFID
<222> LOCATION: (1)..(5)

```
<223> OTHER INFORMATION: Disulfide bond between N-terminal and
      C-terminal Cys

<400> SEQUENCE: 11

Cys Trp Trp Arg Cys
1               5

<210> SEQ ID NO 12
<211> LENGTH: 7
<212> TYPE: PRT
<213> ORGANISM: Artificial sequence
<220> FEATURE:
<223> OTHER INFORMATION: Synthetic cyclic peptide
<220> FEATURE:
<221> NAME/KEY: Acetylation
<222> LOCATION: (1)..(1)
<223> OTHER INFORMATION: Acetylation of Lys
<220> FEATURE:
<221> NAME/KEY: BINDING
<222> LOCATION: (3)..(7)
<223> OTHER INFORMATION: Amide bond between alpha, beta diaminopropionic
      acid in position 3 and C-terminal glutamic acid residue
<220> FEATURE:
<221> NAME/KEY: MISC_FEATURE
<222> LOCATION: (3)..(3)
<223> OTHER INFORMATION: Xaa is alpha, beta diaminopropionic acid

<400> SEQUENCE: 12

Lys Gly Xaa Phe His Arg Glu
1               5

<210> SEQ ID NO 13
<211> LENGTH: 7
<212> TYPE: PRT
<213> ORGANISM: Artificial sequence
<220> FEATURE:
<223> OTHER INFORMATION: Synthetic cyclic peptide
<220> FEATURE:
<221> NAME/KEY: Acetylation
<222> LOCATION: (1)..(1)
<223> OTHER INFORMATION: Acetylation of N-terminal Lys
<220> FEATURE:
<221> NAME/KEY: Bonding
<222> LOCATION: (3)..(7)
<223> OTHER INFORMATION: Amide bond between alpha, beta diaminopropionic
      acid in position 3 and C-terminal glutamic acid residue
<220> FEATURE:
<221> NAME/KEY: MISC_FEATURE
<222> LOCATION: (3)..(3)
<223> OTHER INFORMATION: Xaa is alpha, beta diaminopropionic acid
<220> FEATURE:
<221> NAME/KEY: AMIDATION
<222> LOCATION: (7)..(7)
<223> OTHER INFORMATION: N Amidation of C-terminal glutamic acid

<400> SEQUENCE: 13

Lys Gly Xaa Phe His Arg Glu
1               5

<210> SEQ ID NO 14
<211> LENGTH: 5
<212> TYPE: PRT
<213> ORGANISM: Artificial sequence
<220> FEATURE:
<223> OTHER INFORMATION: Synthetic cyclic peptide
<220> FEATURE:
<221> NAME/KEY: DISULFID
<222> LOCATION: (1)..(5)
<223> OTHER INFORMATION: Disulfide bonding between Nt and Ct Cys
<220> FEATURE:
<221> NAME/KEY: Acetylation
<222> LOCATION: (1)..(1)
<223> OTHER INFORMATION: Acetylation of N terminal Cys
```

```
<400> SEQUENCE: 14

Cys Trp His Arg Cys
1               5

<210> SEQ ID NO 15
<211> LENGTH: 5
<212> TYPE: PRT
<213> ORGANISM: Artificial sequence
<220> FEATURE:
<223> OTHER INFORMATION: Synthetic cyclic peptide
<220> FEATURE:
<221> NAME/KEY: Bonding
<222> LOCATION: (1)..(5)
<223> OTHER INFORMATION: Disulfide bonding between Nt and Ct Cys
<220> FEATURE:
<221> NAME/KEY: Acetylation
<222> LOCATION: (1)..(1)
<223> OTHER INFORMATION: Acetylation of N-terminal Cys

<400> SEQUENCE: 15

Cys Phe Phe Arg Cys
1               5

<210> SEQ ID NO 16
<211> LENGTH: 7
<212> TYPE: PRT
<213> ORGANISM: Artificial sequence
<220> FEATURE:
<223> OTHER INFORMATION: Synthetic cyclic peptide
<220> FEATURE:
<221> NAME/KEY: DISULFID
<222> LOCATION: (1)..(5)
<223> OTHER INFORMATION: Disulfide bonding between Nt Cys and Cys in
      position 5

<400> SEQUENCE: 16

Cys Trp His Arg Cys Ala Arg
1               5

<210> SEQ ID NO 17
<211> LENGTH: 5
<212> TYPE: PRT
<213> ORGANISM: Artificial sequence
<220> FEATURE:
<223> OTHER INFORMATION: Synthetic cyclic peptide
<220> FEATURE:
<221> NAME/KEY: DISULFID
<222> LOCATION: (1)..(5)
<223> OTHER INFORMATION: Disulfide bonding between Nt and Ct Cys
<220> FEATURE:
<221> NAME/KEY: ACETYLATION
<222> LOCATION: (1)..(1)
<223> OTHER INFORMATION: Acetylation of N-terminal Cys

<400> SEQUENCE: 17

Cys Trp Tyr Arg Cys
1               5

<210> SEQ ID NO 18
<211> LENGTH: 7
<212> TYPE: PRT
<213> ORGANISM: Artificial sequence
<220> FEATURE:
<223> OTHER INFORMATION: Synthetic cyclic peptide
<220> FEATURE:
<221> NAME/KEY: DISULFID
<222> LOCATION: (1)..(5)
<223> OTHER INFORMATION: Disulfide bonding between Nt Cys and Cys in
      position 5
```

```
<400> SEQUENCE: 18

Cys Phe Phe Arg Cys Ala Arg
1               5

<210> SEQ ID NO 19
<211> LENGTH: 5
<212> TYPE: PRT
<213> ORGANISM: Artificial sequence
<220> FEATURE:
<223> OTHER INFORMATION: Synthetic cyclic peptide
<220> FEATURE:
<221> NAME/KEY: DISULFID
<222> LOCATION: (1)..(5)
<223> OTHER INFORMATION: Disulfide bonding between Nt and Ct Cys
<220> FEATURE:
<221> NAME/KEY: ACETYLATION
<222> LOCATION: (1)..(1)
<223> OTHER INFORMATION: Acetylation of N terminal Cys
<220> FEATURE:
<221> NAME/KEY: AMIDATION
<222> LOCATION: (5)..(5)
<223> OTHER INFORMATION: Amidation of C terminal Cys

<400> SEQUENCE: 19

Cys Trp Tyr Arg Cys
1               5

<210> SEQ ID NO 20
<211> LENGTH: 5
<212> TYPE: PRT
<213> ORGANISM: Artificial sequence
<220> FEATURE:
<223> OTHER INFORMATION: Synthetic cyclic peptide
<220> FEATURE:
<221> NAME/KEY: DISULFID
<222> LOCATION: (1)..(5)
<223> OTHER INFORMATION: Disulfide bonding between Nt and Ct Cys
<220> FEATURE:
<221> NAME/KEY: AMIDATION
<222> LOCATION: (5)..(5)
<223> OTHER INFORMATION: Amidation of C terminal Cys

<400> SEQUENCE: 20

Cys Trp His Arg Cys
1               5

<210> SEQ ID NO 21
<211> LENGTH: 5
<212> TYPE: PRT
<213> ORGANISM: Artificial sequence
<220> FEATURE:
<223> OTHER INFORMATION: Synthetic cyclic peptide
<220> FEATURE:
<221> NAME/KEY: DISULFID
<222> LOCATION: (1)..(5)
<223> OTHER INFORMATION: Disulfide bonding between Nt and Ct Cys
<220> FEATURE:
<221> NAME/KEY: AMIDATION
<222> LOCATION: (5)..(5)
<223> OTHER INFORMATION: Amidation of C terminal Cys

<400> SEQUENCE: 21

Cys Trp Tyr Arg Cys
1               5

<210> SEQ ID NO 22
<211> LENGTH: 5
<212> TYPE: PRT
<213> ORGANISM: Artificial sequence
```

```
<220> FEATURE:
<223> OTHER INFORMATION: Synthetic cyclic peptide
<220> FEATURE:
<221> NAME/KEY: DISULFID
<222> LOCATION: (1)..(5)
<223> OTHER INFORMATION: Disulfide bonding between Nt and Ct Cys

<400> SEQUENCE: 22

Cys Arg His Trp Cys
1               5

<210> SEQ ID NO 23
<211> LENGTH: 8
<212> TYPE: PRT
<213> ORGANISM: Artificial sequence
<220> FEATURE:
<223> OTHER INFORMATION: Synthetic cyclic peptide
<220> FEATURE:
<221> NAME/KEY: DISULFID
<222> LOCATION: (4)..(8)
<223> OTHER INFORMATION: Disulfide bonding between Cys in position 4 and
      Ct Cys

<400> SEQUENCE: 23

Arg Pro Ala Cys Arg Phe Phe Cys
1               5

<210> SEQ ID NO 24
<211> LENGTH: 8
<212> TYPE: PRT
<213> ORGANISM: Artificial sequence
<220> FEATURE:
<223> OTHER INFORMATION: Synthetic cyclic peptide
<220> FEATURE:
<221> NAME/KEY: DISULFID
<222> LOCATION: (4)..(8)
<223> OTHER INFORMATION: Disulfide bond between Cys in position 4 and Ct
      Cys

<400> SEQUENCE: 24

Lys Ala Pro Cys Arg Phe Phe Cys
1               5
```

CYCLIC PEPTIDES BINDING CXCR4 RECEPTOR AND RELATIVE MEDICAL AND DIAGNOSTIC USES

Figure 1:
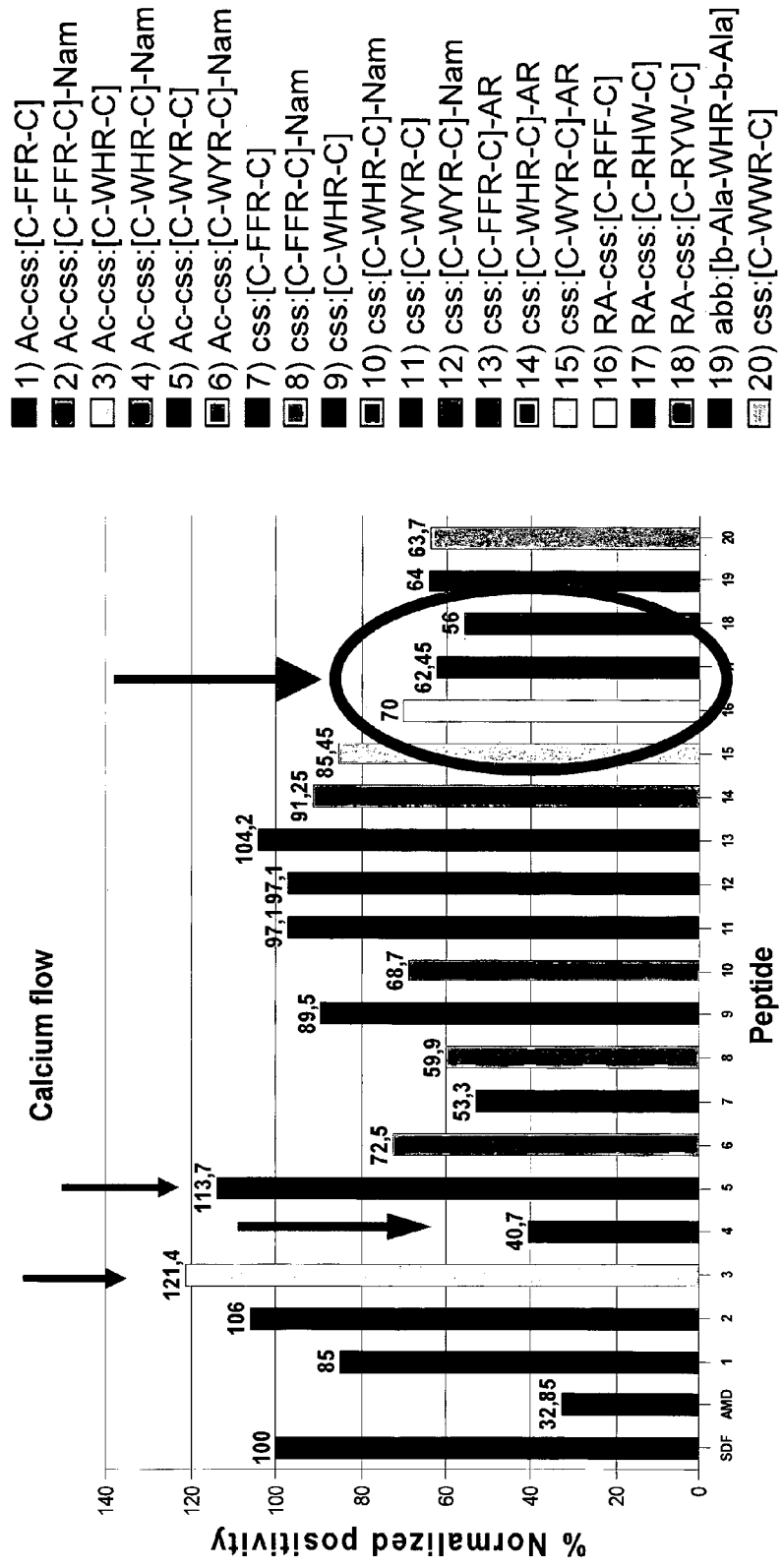

The present invention relates to the identification of new peptides and peptidomimetics which bind the CXCR4 receptor, capable of forming complexes with receptors for chemokines, in particular with CXCR4. The invention also relates to the use of these peptides for the treatment, prevention and diagnosis of diseases which involve chemokine receptors (i.e. neoplasias, metastases, HIV-1 virus infections), and also the mobilization of stem cells of hemopoietic precursors in the case of autologous transplants. Finally, the invention comprises pharmaceutical compositions and diagnostic kits comprising said peptides.

Chemokines are a family of small proteins of 8-10 kDa with a chemotactic activity. They are characterized by a wide range of biological activities, including the regulation of leukocyte trafficking, modulation of hemopoietic cell proliferation and adhesion to the extra-cellular matrix molecules.

A role of the chemokine-receptor axis for chemokines in human neoplasias has been recently identified. The CXCR4 receptor and relative chemokine, CXCL12, have been mainly described in numerous neoplasias.

CXCL12 is a chemokine of the type C-X-C which interacts with a specific receptor, CXCR4, belonging to the group of transmembrane receptors coupled with G proteins (GPCR). GPCRs are characterised by a common central domain consisting of seven transmembrane helixes, connected by three intracellular loops (i1, i2 and i3) and by three extracellular loops (e1, e2 and e3). Two cysteine residues (one on the helix 3 and the other on the loop e2), which are preserved in most GPCRs, form an important disulfide bridge for the packing and stabilization of the helicoidal domain. Apart from the sequence variability, GPCRs differ in the length and function of the N-terminal extracellular domain, the C-terminal intracellular domain and the intracellular loops.

For a long time it was believed that GPCRs were functionally active monomeric species and only recently, thanks to numerous experimental demonstrations and combined approaches, is the concept being affirmed that GPCRs are biologically active as dimers or higher oligomers. The capacity of GPCRs of homo- or hetero-oligomerizing is a necessary requisite for the function and it is obviously not a random process: the selective dimerization defines the pharmacology of the ligand and the biological response.

An extremely controversial question is how the ligands of these receptors alter the dimerization or structural organization of GPCRs and whether or not the pharmacology of the ligands or function of the heterodimers is different from that of homodimers. Recent studies have shown that the stoichiometry of the receptors with respect to the G protein is at least 2:1, whereas the mode with which each receptor in the dimer (or in the oligomer) interacts with the subunits Gα and Gβγ of heterotrimeric G protein is still an object of study. An important aspect in the functionality of receptor dimers has been demonstrated by the modification of a receptor subunit made constitutionally active or modified so as to bind an agonist or antagonist not recognized by the second subunit: the activation of the second receptor, once the first has been activated, led to a loss of the signal, whereas its inhibition promoted an increase in the signal. The activity of a homodimeric receptor can therefore be allosterically controlled by means of a differential binding to each receptor unit. This result is also more important in the case of heterodimers and can lead to an interpretation of the multivariate response of the ligands in the different signal pathways of GPCRs. In the case of CXCR4, it is well-known that this receptor can either homo- or hetero-dimerize.

Mammary neoplasia cells express high levels of CXCR4 and the specific chemokine, CXCL12, is predominantly expressed at the level of mammary neoplasia metastases. Treatment with neutralizing antibodies for CXCR4 dramatically reduces the metastasis. Also in the model of melanomas, carcinomas of the colon, renal carcinomas, colon-rectum, lungs, glioblastomas, carcinomas of the prostate, the CXCR4/CXCL12 axis has proved to have a central role in metastatization. Consequently the receptors for chemokines and relative ligands have a crucial role in the metastatization process.

The authors of the present invention have previously demonstrated [1-3] a prognostic role for the expression of the CXCR4 receptor in association with the expression of VEGF in neoplasias of the colon-rectum and a prognostic value for the expression of CXCR4 in primitive melanomas. Considerable experimental evidence suggests that solid tumours are generated and maintained by a small population of tumoral cells capable of proliferating indefinitely and producing a progeny of differentiated cells. The expression of receptors for chemokines, and in particular CXCR4, has been widely described on neoplastic stem cells.

CXCR4 has also been identified as a co-receptor for the fusion and infection of T cells on the part of the HIV-1 virus. The entry of the virus into the host cell is mediated by the interaction of some glycoproteins of the viral involucrum (gp120 and gp41) with receptors of the host cell (CD4 and CCR5 or CXCR4), through a complex sequence of molecular events which begin with the binding of trimers of the viral protein gp120 to the primary receptor CD4. This interaction is not sufficient for promoting the entry of the virus into the cell, but serves for making the binding site for the chemokine receptors accessible on the protein gp120 by the induction of a conformational variation in the glycoprotein. Although different viral subtypes can be bound to different receptors for chemokines, CCR5 and CXCR4 by far represent the most common target for HIV-1. The use of ligands of CXCR4 capable of antagonizing the binding of the viral glycoprotein gp120 to the coreceptors represents a new frontier for the development of anti-AIDS therapeutic agents.

Recent evidence emphasizes the role of the CXCR4-CXCL12 axis in medullary homing and consequently in the mobilization of hemopoietic precursors. In bone marrow and lymphoid tissues, tumoral cells are in direct contact with stromal cells which form the microenvironment relating to the various stages of the disease. CXCL12 has a wide range of effects in relation to the development of neoplasias, but the primary role of CXCL12 is in the mobilization of hemopoietic precursors and in the definition of a niche of neoplastic stem cells in which the high concentration of CXCL12 recalls a subpopulation of highly tumorigenic cells and promotes their survival, proliferation, angiogenesis and metastatic diffusion.

The possibility that the inhibition of the CXCR4-CXCL12 axis influences the availability of hemopoietic precursors was evident through Phase 1 studies in healthy volunteers, before beginning Phase II study in patients affected by AIDS, with the CXCR4 inhibitor, AMD3100(1,19-[1,4-phenylenebis(methylene)]-bis-1,4,8,11-azatetradecane) [4].

In these volunteers, there is a rapid increase in the white blood cell series with a peak 6 hours after the administration of AMD3100. Upon detailed observation, the cells of the white series mobilized expressed the marker CD34 and they were therefore characterized as hemopoietic precursors [3,4].

It was subsequently demonstrated that the combination of AMD3100 in association with G-CSF, a mobilizing agent in use, is safe, effective and better than G-CSF along for the mobilization of hemopoietic precursors in autologous transplants. It also seems that the population mobilized by AMD3100 is different from that mobilized by G-CSF.

Calandra at al. have demonstrated that the combination of AMD3100 and G-CSF mobilizes a sufficient number of CD34+ cells in non-Hodgkin lymphomas, in multiple myelomas and in Hodgkin lymphomas [5].

Although AMD3100, in the light of the data indicated above, proves to be a rapid and effective mobilizing agent, it has revealed in previous studies, however, a poor bioavailability, hepatic, cardiac and cerebellar toxicity [4].

In the light of what is specified above, it would be desirable to identify new molecules capable of exerting a selective action on different pathways associated with the CXCR4-CXCL12 axis causing fewer side-effects, to be advantageously used in the treatment, prevention and diagnosis of illnesses in which chemokine receptors are involved (i.e. neoplasias, metastases, HIV-1 virus), and also to mobilize stem cells of hemopoietic precursors in the case of autologous transplants.

The authors of the present invention have now identified new monomeric or dimeric cyclic peptides to be used in the therapy, prevention and diagnosis of pathologies which are responsive and sensitive to the modulation of the receptor for CXCR4 chemokines (i.e. tumours, metastases, HIV infections), or for the mobilization of hemopoietic precursors in the field of autologous bone marrow transplants.

This receptor is in fact hyper-expressed in the sites of mammary neoplasia metastases. Also in the model of melanomas, carcinomas of the colon, renal carcinomas, of the colon-rectum, lungs, glioblastomas, carcinomas of the prostate, the CXCR4/CXCL12 axis has proved to have a central role in metastatization.

Furthermore, recent evidence emphasizes the role of the CXCR4-CXCL12 axis in medullary homing and consequently in the mobilization of hemopoietic precursors.

CXCR4 has also been identified as a co-receptor for the fusion and infection of T cells on the part of the HIV-1 virus.

The action mechanism of the peptides according to the invention is assumed to regulate the activity of CXCR4 receptors by competition with the endogen chemokine CXCL12 for the orthosteric binding sites, but the possibility that they act as allosteric effectors is not excluded. Consequently the selected peptides, object of the invention, show the biological and pharmacological activities of the compounds capable of selectively biding the CXCR4 receptor, useful both as antitumoral agents and as drugs capable of facilitating the mobilization of hemopoietic precursors in the field of autologous bone marrow transplants.

The capacity of the peptides of the invention of binding the CXCR4 receptor, regardless of their agonist or antagonist activity, also makes them valid candidates as diagnostic markers for neoplastic pathologies.

The peptides of the invention could be potentially useful as prophylactic anti-AIDS agents, as they can potentially compete for the binding to the CXCR4 receptor with the viral glycoprotein gp120.

An object of the present invention therefore relates to monomeric peptides containing up to nine amino acids characterised in that they have a modulatory activity on the CXCR4 receptor having the following general formula (I):

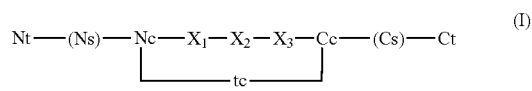

wherein:
the N- terminal group Nt of the peptide is selected from free ammonium, acetyl (Ac), formyl (Fo) and tert-butoxycarbonyl (tBoc);
the C terminal group Ct of the peptide is selected from free carboxylate, primary amide (Nam), N-methylamide (NMe), methyl ester (Ome);
the N terminal sequence (Ns) optionally present has a formula selected between B-x-; B-x-x- and B-x-x-x-;
the C terminal sequence (Cs) optionally present has a formula selected between -x-B; -x-x-B and -x-x-x-B;
wherein B represents an encoded basic amino acid residue selected from lysine (K) and arginine (R), or non-encoded, and wherein x represents any encoded or non-encoded amino acid residue; wherein said sequences (Ns) and (Cs) may be present with mutual exclusion or both absent;
the amino acid residues Nc and Cc, the same or different each other, are selected from the group consisting of cysteine (C), glutamic acid (E), β-Alanine (β-Ala), α,β diaminopropionic acid (Dap), α,γ diaminobutyric acid (Dab), ornithine (Orn);
the bond tc that involves the amino acid residues Nc and Cc in the ring formation is selected from the group consisting of disulphide bridge between cysteine side chains (css), backbone-side chain amide bond (abs) and vice-versa (asb), amide bond between side chains (asc), peptide bond via main chain (abb), backbone-side chain ester bond (ebs) and vice-versa (esb), ester bond between side chains (esc);
the central sequence $X_1$-$X_2$-$X_3$ is selected from $Ar_1$-$Ar_2$-B and B-$Ar_2$-$Ar_1$, wherein B is an encoded basic amino acid residue selected from lysine (K) and arginine (R), or non-encoded, and $Ar_1$-$Ar_2$ are encoded aromatic residues selected from phenylalanine (F), tryptophan (W), tyrosine (Y) and histidine (H), or no-encoded ones; or pharmacologically acceptable salts thereof.

A monomeric peptide according to the invention preferably consists of from 5 to about 9 amino acid residues. More preferably, the cyclic region of the peptide is composed of not more than 5 amino acid residues.

A pharmacologically acceptable salt of one of the peptides in question can be easily prepared starting from a peptide (or one of its peptidomimetic analogues) by means of conventional methods. Said salt can be prepared, for example, by treatment of the peptide with an aqueous solution of the desired pharmacologically acceptable metal hydroxide or another metal base and subsequently allowing the residual solution to evaporate until it is dry, preferably under reduced pressure conditions in a nitrogen atmosphere. Alternatively, a solution of a peptide can be mixed with an alkoxide of the desired metal, and the solution is subsequently evaporated until it is dry.

The term "pharmacologically acceptable salt" refers to bases added to non-toxic acids, inorganic anion contributors, such as chloride, bromide, phosphate, sulfate, perchlorate, nitrate, or organic anions such as acetate, oxalate, maleate, malate, tartrate, citrate, succinate, malonate, formiate, lactate, p-toluenesulfate, or acids added to non-toxic bases, cation contributors which include, but not exclusively, those based on alkalis or alkaline-earth metals, such as sodium, lithium, potassium, calcium, magnesium and the like, and also non-toxic ammonium, quaternary ammonium and cationic amines, including, but not exclusively, ammonium, tetramethylammonium, tetraethylammonium, methylamine, dimethylamine, trimethylamine, triethylamine, ethylamine, and the like.

According to preferred embodiments of the present invention, the N terminal sequence Ns is: a) absent; b) the dipeptide RA, RP, RG, KA, KP o KG; c) tripeptide RPA, KPA, RAP or KAP.

According to preferred embodiments of the present invention, the C terminal sequence Cs is: a) absent; b) the dipeptide AR, PR, GR, AK, PK o GK; c) the tripeptide APR, APK, PAR or PAK.

Said central sequence $X_1$-$X_2$-$X_3$ preferably selected from RHW, RFF, WHR, FHR, RHF, FYR, RYF, FFR, WYR, RYW, WFR, RFW.

According to preferred embodiments, the peptides having formula (I) having a modulating activity on the CXCR4 receptor can be selected from the group consisting in:

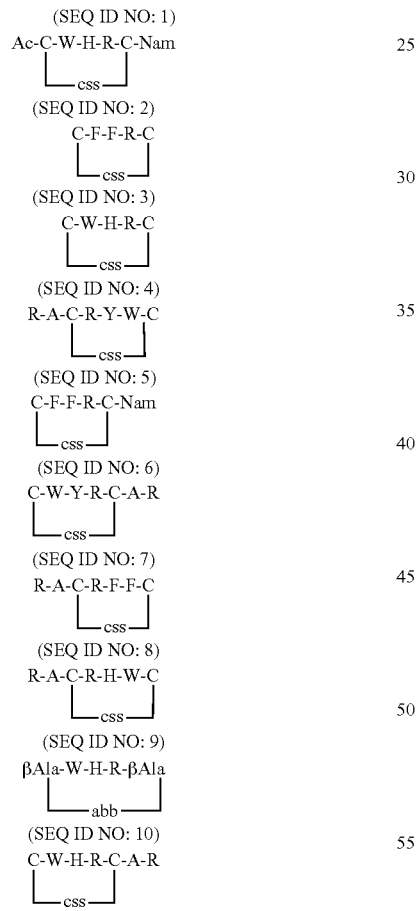

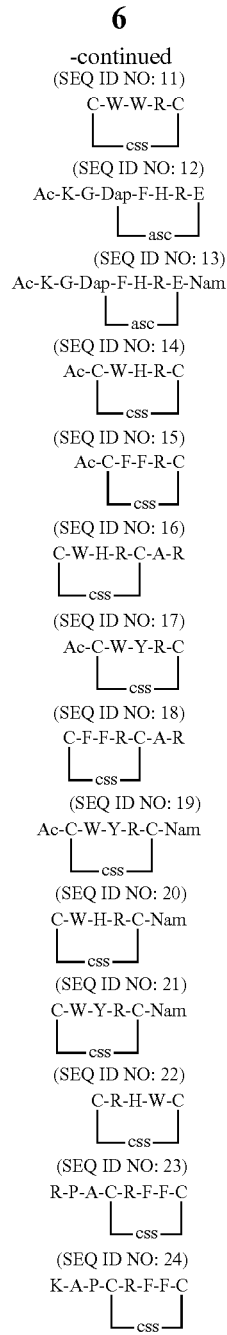

The peptides of the invention comprise both monomeric and dimeric cyclic peptides, their combinations and pharmacologically acceptable salts.

An object of the present invention relates to homodimers and heterodimers between two peptides having formula (I) as previously defined, selected from the group consisting in:
a) tail-head or head-tail dimers having the following general formula (II):

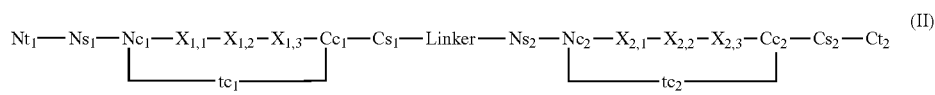

b) tail-tail dimers having the following general formula (III):

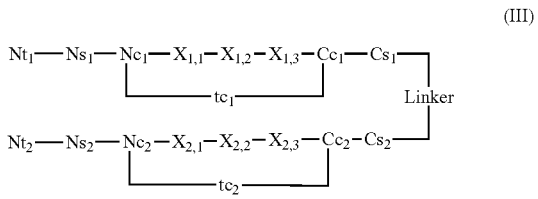

(III)

c) head-head dimers having the following general formula (IV):

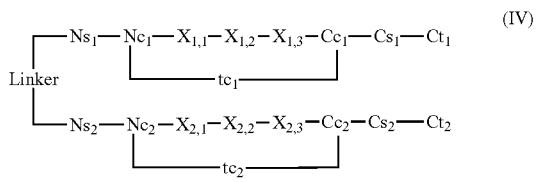

(IV)

wherein $Nt_1$, $Ns_1$, $Nc_1$, $Cc_1$, $Cs_1$, $Ct_1$, $X_{1,1}$, $X_{1,2}$, $X_{1,3}$ are relative to the first peptide and have the same meaning indicated above; wherein $Nt_2$, $Ns_2$, $Nc_2$, $Cc_2$, $Cs_2$, $Ct_2$, $X_{2,1}$, $X_{2,2}$, $X_{2,3}$ are relative to the second peptide and have the same meaning indicated above;
wherein the bond between said first peptide and said second peptide occurs through substitution of the terminal groups $Nt_1$ and $Nt_2$, $Ct_1$ and $Ct_2$, $Nt_1$ and $Ct_2$ or $Ct_1$ and $Nt_2$ with a linker group selected from polyethylene glycol (PEG), hexamethylenediamine (N6), PEG600, PEG300-aminomalonyl-PEG300. These hydrosoluble molecules serve to give the peptides of the invention a greater bioavailability, solubility and stability, in addition to reducing their immunogenicity.

Dimeric peptides exert the same therapeutic effects as the monomer peptides of the invention.

The term "peptide" is used to indicate a polymeric molecule consisting of a relatively low number of amino acids (lower than 100 residues) joined by a peptide binding. When an amino acid is inserted in a peptide chain, it is called "amino acid residue". The peptide chain is characterised by two ends, the "head" and "tail", not engaged in a peptide binding: the head is the N-terminal end which has a free amine group, whereas the tail is the C-terminal end and carries a free carboxyl group.

The term "main chain" or "backbone" is used to indicate the amino acid portion consisting of the atoms which form the peptide binding i.e. the carbonyl carbon atom, the oxygen atom, the nitrogen atom and carbon atom in alpha position.

The term "sidechain" relates to the variable part of each amino acid, capable of conferring specific chemical characteristics to each residue, on the basis of which they are classified as: 1) aromatic: phenylanine (F), tryptophan (W), tyrosine (Y) and histidine (H); 2) positively charged: lysine (K) and arginine (R); 3) negatively charged: aspartic acid (D) and glutamic acid (E); 4) polar: asparagine (N), glutamine (O), treonine (T), serine (S) and 5) hydrophic: valine (V), leucine (L) isoleucine (I), alanine (A), methionine (M), cysteine (C), glycine (G), Proline (P).

With the exception of glycine, amino acids are chiral molecules, characterised by the presence of an asymmetrical alpha carbon atom. They are marked by the letters L or D depending on whether substituents of the chiral carbon atom have an arrangement similar to that of L-glyceraldehyde or that of D-glyceraldehyde.

The term "encoded" amino acid refers to one of the twenty amino acids encoded in the genetic code for protein synthesis, the term "non-encoded" refers to amino acids not encoded in the genetic code and obtained in nature by means of post-translational modifications and/or other biosynthetic pathways different from protein synthesis or artificially, by means of chemical synthesis processes.

According to alternative embodiments of the present invention, derivatives of monomeric or dimeric peptides having formula (I)-(IV) can be used, wherein said peptides are functionalized by a covalent bond of fluorescent, chemiluminescent, magnetic or radioactive groups (i.e. radiomarkers such as $^{125}I$, $^{32}P$ o $^{35}S$) at the level of the main chain, side chains or linker group. The detectable group can also be a detectable protein group, i.e. a testable enzyme or an antibody epitope. Analogously, the detectable group can be a substrate, a cofactor, an inhibitor or an affinity ligand.

The invention relates to peptides characterised in that they have an agonist activity on the CXCR4 receptor, which stimulate the repopulation of the ischemic tissues at a cardiac and neuronal level [6-12], selected from the group which consists in:

(SEQ ID NO: 14)

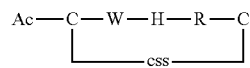

(SEQ ID NO: 15)

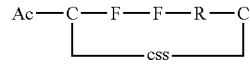

(SEQ ID NO: 16)

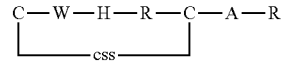

(SEQ ID NO: 17)

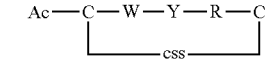

(SEQ ID NO: 18)

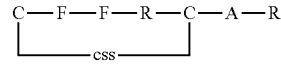

(SEQ ID NO: 19)

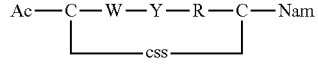

(SEQ ID NO: 20)

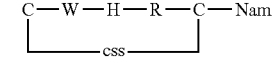

(SEQ ID NO: 21)

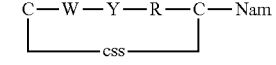

Although the peptides of the invention are described mainly using the term "peptide" or "peptides", an expert in the field, when reading the present description, will understand that these terms also include structural analogues and derivatives of the peptides described above. For example, together with the peptides described above, which can comprise amino acids present in nature, there are also peptidomimetics of the peptides according to the present invention. Peptide analogues are commonly used in the pharmaceutical industry as non-peptide drugs with analogous properties to those of peptide templates. These types of non-peptide compounds are called "mimetic peptides" or "peptidomimetics" and are usually developed with the help of computerized molecular modeling [16-18].

Mimetic peptides which are structurally similar to peptides that are advantageous from a therapeutic or prophylactic point of view, can be used for producing an equivalent therapeutic or prophylactic effect. Peptidomimetics are generally structurally similar to a model peptide (i.e. a peptide which has a biological or pharmacological activity), but they have one or more peptide bonds optionally substituted by a bond selected from the group which consists of: —$CH_2 NH_2$—, —$CH_2S$—, —$CH_2$—$CH_2$—, —CH=CH— (cis and trans), —$COCH_2$—, —$CH(OH)CH_2$—, and —$CH_2SO$—. These peptidomimetics can be generated by means of the methods known in the art and further described in the bibliographical references [19]-[29] cited hereunder.

Mimetic peptides can have significant advantages with respect to mimed peptides, including, for example: more economical production; greater chemical stability; improved pharmacological properties (half-life, absorption, power, effectiveness); altered specificity (i.e. a wide range of biological activities); reduced antigenicity.

Due to their capacity of binding the receptor for CXCR4 chemokines and exerting an agonist or antagonist action on the functionality of the receptor, the peptides of this invention are advantageously used for the treatment or prevention of a wide range of diseases and disturbances which respond or are sensitive to the modulation of the activity of the CXCR4 receptor.

An object of the present invention therefore relates to the use of at least one monomeric or dimeric peptide having formula (I)-(IV), or their derivatives, or mixtures thereof, for the preparation of a medicament for the treatment and prevention of tumours or relapses/metastases in tumoral pathologies whose cells overexpress the receptor for chemokines CXCR4.

Said tumours are preferably selected from the group which consists in neoplasias of the breast, colon, stomach, glioblastomas and melanomas [13, 14].

A further object of the present invention relates to the use of at least one monomeric or dimeric peptide having formula (I)-(IV), or their derivatives, or mixtures thereof, for the preparation of a medicament for the treatment and prevention of HIV-1 infections from viral subtypes which use receptors for chemokines of the host cell, as co-receptors.

The invention also relates to the use of monomeric or dimeric peptides having formula (I)-(IV), or their derivatives, or mixtures thereof, for the preparation of a medicament in the therapy of bone marrow trans-plants for the mobilization of the stem cells. The mobilization of hematopoietic precursors is in fact necessary in the area of autologous bone marrow trans-plants in subjects necessitating this.

The term "subject" is used for indicating an animal, such as a mammal, including human beings. Non-human animal subjects to be treated include, for example, fish, birds and mammals such as cattle, sheep, swine, horses, dogs and cats.

The invention also relates to the use of monomeric or dimeric peptides having formula (I)-(IV) as tumoral markers.

This diagnosis can be effected in vivo by the administration of an effective quantity of a suitably marked peptide of the invention, in a subject.

The invention also relates to pharmaceutical compositions comprising at least one of the monomeric or dimeric peptides having formula (I)-(IV), their derivatives, or mixtures thereof, as active principle together with one or more excipients or pharmacologically acceptable carriers.

The term "pharmacologically acceptable carrier" comprises any carrier, buffers and excipients, pharmacological standard, which comprise a buffer-phosphate saline solution, water, and emulsions (such as an oil/water or water/oil emulsion), and various types of wetting agents and/or adjuvants. Pharmacologically acceptable carriers and their formulations are described in [30]. Pharmacologically preferred carriers depend on the administration mode of the active agent proposed. Typical administration modes are oral, endovenous, intramuscular, rectal, subcutaneous.

The invention provides pharmaceutical compositions in the form of a single dosage which comprise a pharmacologically acceptable carrier per dosage unit within a range of 0.01 milligrams (mg) to about 1,000 mg of the peptides of the invention or their pharmacologically acceptable salts. In a preferred aspect, the invention provides pharmaceutical compositions in the form of a single dosage comprising a pharmacologically acceptable carrier per dosage unit and a range of about 1 mg to about 100 mg of the peptides of the invention or their pharmacologically acceptable salts. According to another aspect, the invention provides peptide polymers which comprise at least two peptides.

The preselected form of these pharmaceutical compositions depends on how they are to be administered and on the therapeutic application. The compositions can comprise, depending on the desired formulation, pharmacologically acceptable, non-toxic carriers or diluents, which are defined as vehicles commonly used in the formulation of pharmaceutical compositions for human or animal administration.

The peptides according to the invention are hydrosoluble at the low concentrations in which they are typically used. These peptides are preferably used in the form of their acid or alkaline salts formed with pharmacologically acceptable agents, such as acetic acid, citric acid, maleic acid, or succinic acid. The soluble salts without the peptides in question can also be converted into salts with a low solubility in body fluids by modification with a slightly hydrosoluble pharmacologically acceptable salt (such as tannic acid or palmoic acid), by inclusion in a formulation with controlled release of the peptide (such as through covalent coupling with a larger protein carrier or a peptide), or by inclusion in capsules with controlled release and similar products. The acid salts of the peptides of the invention are generally biologically and pharmacologically equivalent to the same peptides.

In some cases, it may be advisable to stabilize the monomeric or dimeric peptides according to the invention and their analogues or derivatives to increase their half-life and the pharmacokinetic half-life. The stability of the half-life is improved by adding excipients such as: a) hydrophobic agents (i.e. glycerol); b) sugars (i.e. sucrose, mannose, sorbitol, ramnose, or xylose); c) complex carbohydrates (i.e. lactose); and/or d) bacteriostatic agents. The pharmacokinetic half-life of the peptides in question can be modified by coupling with carrier peptides, polypeptides, and carbohydrates using chemical derivatization (i.e. by coupling a side chain or N- or C-terminal residues), or chemically altering an amino acid of the peptide in question. The pharmacokinetic half-life and pharmacodynamics of these peptides can also be modified by: a) encapsulation (i.e. in liposomes); b) control of the hydration degree (i.e. by controlling the entity and type of glycosylation of the peptide; and c) control of the electrostatic charge and hydrophobicity of the peptide.

Finally, the invention contemplates kits for the diagnosis of tumoral pathologies comprising one or more monomeric or dimeric peptides having formula (I)-(IV) and/or their derivatives.

For some applications in the diagnostic field, it may be desirable to provide the peptides of the invention as marked entities, i.e. covalently attached or bound to a detectable group, to facilitate the identification, detection and quantification of the peptide in a certain circumstance. These detectable groups can comprise a detectable protein group, i.e. a testable enzyme or an antibody epitope. Alternatively, the detectable group can be selected from a variety of other detectable groups or markers, such as radiomarkers (i.e., $^{125}$I, $^{32}$P or $^{35}$S) or a chemiluminescent or fluorescent group. Analogously, the detectable group can be a substrate, a co-factor, an inhibitor or an affinity ligand.

The present invention will now be described for illustrative and non-limiting purposes, according to its preferred embodiments with particular reference to the figures of the enclosed drawings, in which:

FIG. 1 shows the evaluation of calcium release in CCFR-CEM cells in the presence of CXCL12 and peptide inhibitors of CXCR4; CCFR-CEM (500,000 cells) resuspended in 1 ml of Loading Buffer (PBS 1×, 1 mM CaCl$_2$, 1 mM MgCl$_2$, 1% FBS inactivated with heat) at 37° C., and incubated with 4 ul of calcium tracer FLUO3-AM (1 mg/ml; Sigma) and 4 ul of pluronic acid F-127 (1 mg/ml in 2% of DMSO; Invitrogen) in the dark for 30' at 37° C. under stirring. The specific inhibitor of CXCR4 AMD3100 or the peptide tested is added at a concentration of 10 uM; incubation in the dark (15 minutes at room temperature) followed by cytofluorimetric analysis: Ac-css:[C-WHR-C]-Nam reduces Calcium release by 40.7%, css:[C-FFR-C] by 53.3%, css:[C-FFR-C]-Nam by 59.9% and RA-css:[C-RYW-C] by 56%.

Figure 2:
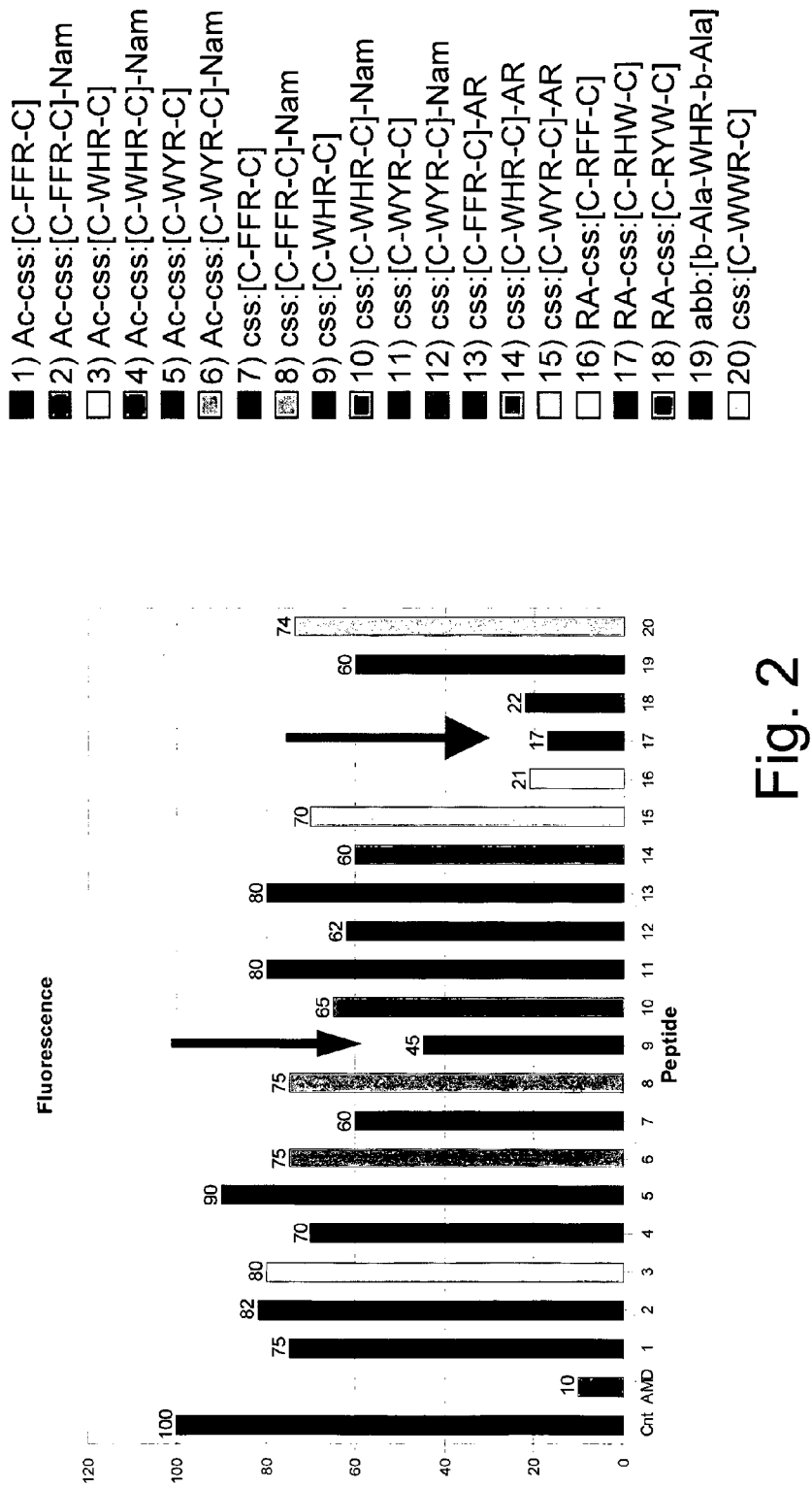

FIG. 2 shows the evaluation of the binding to the CXCR4 receptor in the presence of specific peptides inhibiting CXCR4 (css:[C-WHR-C], RA-css:[C-RFF-C], RA-css:[C-RHW-C], RA-css:[C-RYW-C]). The CCRF-CEM cells were pre-incubated with each peptide for 30' and then incubated again in the presence of the antibody anti-CXCR4. In order to verify the number of receptor molecules available for the anti-CXCR4 antibody, a test was used which allows the number of fluorescent antibodies bound to the cell to be quantified by comparison through the known value of fluorescent spheres conjugated with phycoerythrin.

Figure 3:
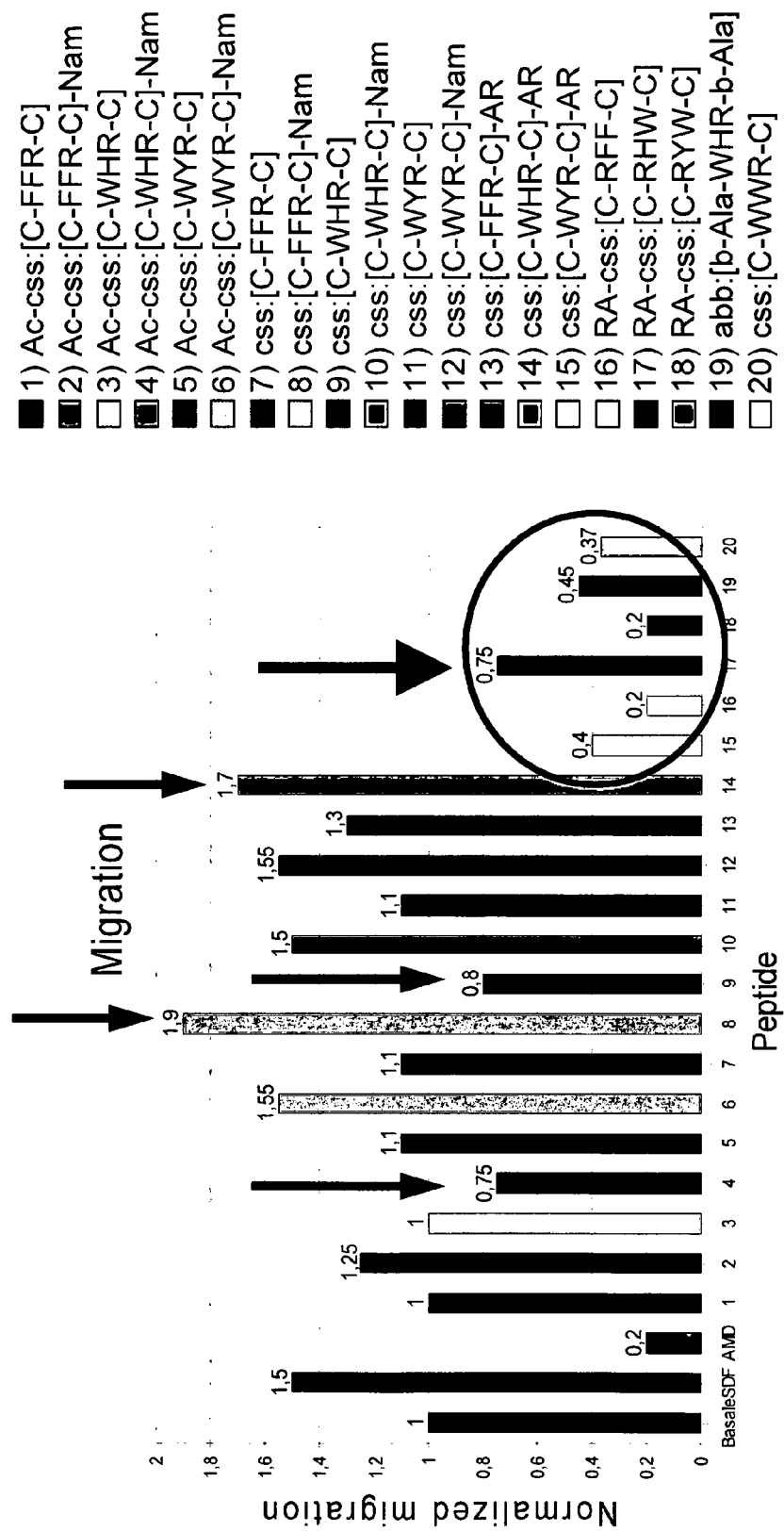

FIG. 3 shows the results of the migration test in the presence of CXCL12 and specific peptides inhibiting CXCR4 according to the invention (css:[C-WHR-C]; css:[C-WYR-C]-AR; RA-css:[C-RFF-C]; RA-css:[C-RHW-C]; RA-css:[C-RYW-C]; abb:[β-Ala-WHR-β-Ala]; css:[C-WWR-C]; css:[C-FFR-C]-Nam and css:[C-WHR-C]-AR), using a human melanoma cell line, PES43 previously characterized by expression of CXCR4 and migratory capacity in response to increasing concentrations of CXCL12. The migration index was defined as the ratio between the migration of the cells of the experimental group divided by the control group. The positive control of the experiment consists in the migration of the cells towards serum.

Figure 4:
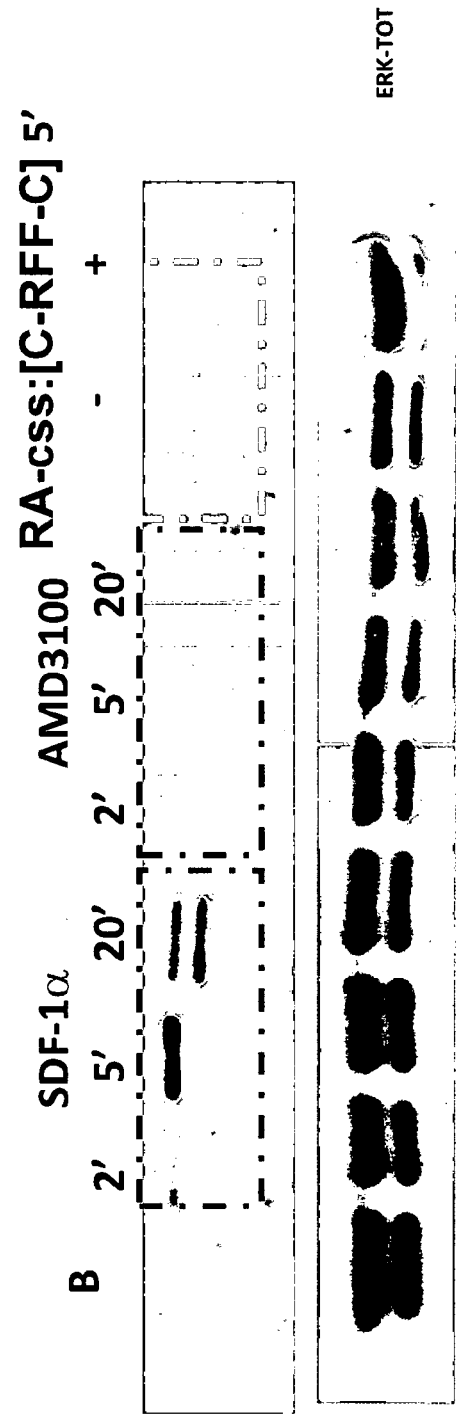

FIG. 4 shows the results of the evaluation assay of p-ERK induction by means of Immunoblotting in the presence of CXCL12 and specific concentrations of peptides inhibiting CXCR4 according to the invention (css:[C-WHR-C] (10 uM), css:[C-FFR-C] (10 uM), css:[C-FFR-C]-Nam (10 uM), css:[C-WYR-C]-AR (10 uM), RA-css:[C-RFF-C] (10 uM), RA-css:[C-RHW-C] (10 uM), abb:[β-Ala-WHR-β-Ala] (10 uM). Human melanoma cells, PES43, grown on 100 mm plates, were treated with SDF-1α, for 2-5-7-10 minutes. Through this experiment, it was observed that SDF-1α is capable of inducing the phosphorylation of ERK 1, 2 at 2 and 5 minutes. CXCL12 activates the phosphorylation of ERK and this phosphorylation is inhibited by both AMD3100 (1 uM), and by the peptides css:[C-WHR-C] (10 uM), css:[C-FFR-C] (10 uM), css:[C-FFR-C]-Nam (10 uM), css:[C-WYR-C]-AR (10 uM), RA-css:[C-RFF-C] (10 uM), RA-css:[C-RHW-C] (10 uM), abb:[β-Ala-WHR-β-Ala] (10 uM).

Figure 5:
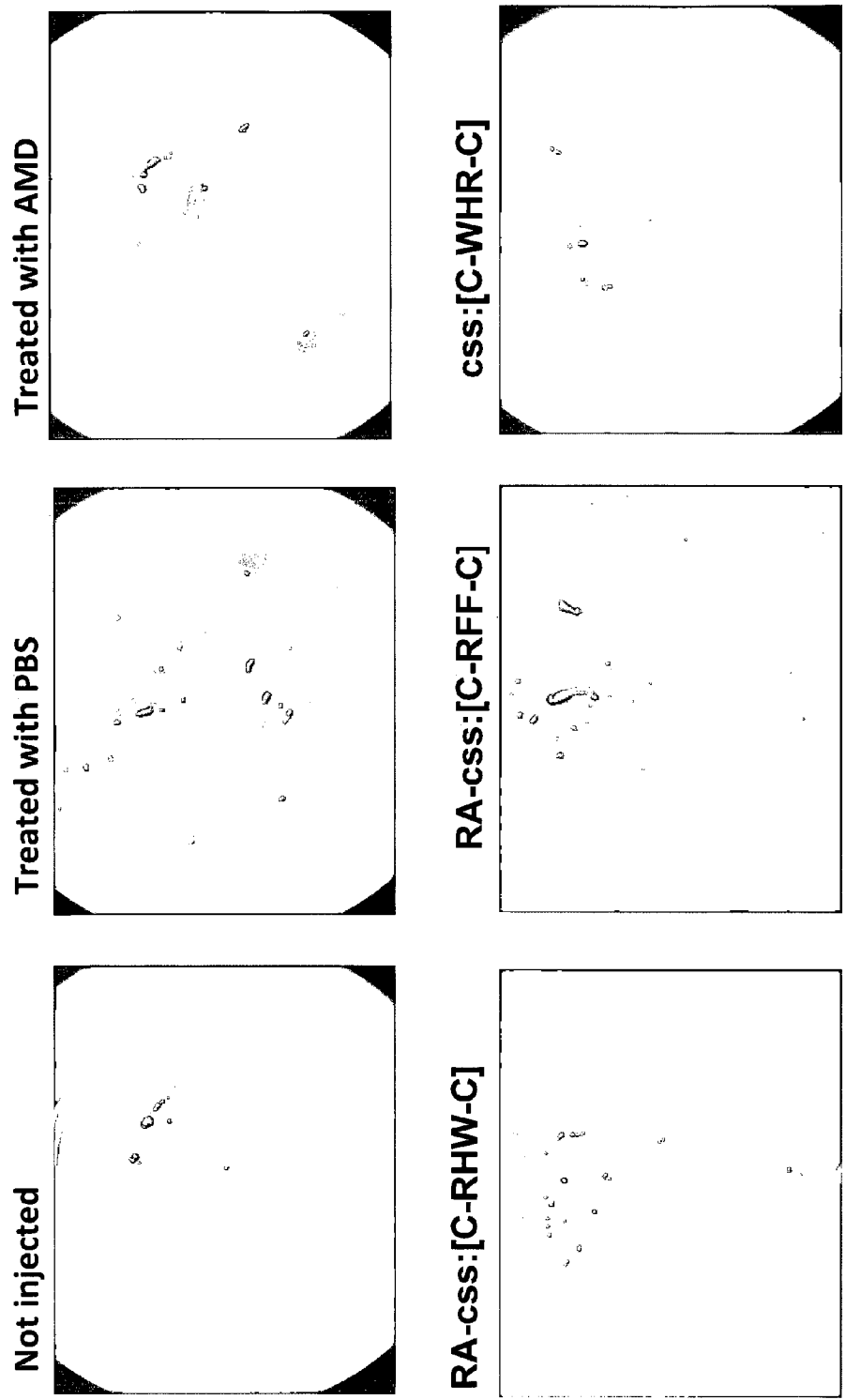

FIG. 5 shows microscopic and macroscopic analysis of melanoma lung metastasis effected on 25 female mice C57/B, between the sixth and eighth week of life and with a weight of about 18 g. The mice were divided into 5 groups, each containing 5 mice, depending on the specific treatment: GROUP A: treatment with 100 μL PBS; GROUP B: treatment with 1.25 mg/Kg AMD 3100 in 100 μL of PBS; GROUP C: treatment with 2 mg/Kg RA-css:[C-RHW-C] in 100 μL of PBS; GROUP D: treatment with 2 mg/Kg RA-css:[C-RFF-C] in 100 μL of PBS; GROUP E: treatment with 2 mg/Kg css:[C-WHR-C] in 100 μL of PBS.

The present invention is further illustrated through the following examples. These examples are purely illustrative of the present invention and should not be considered as limiting the scope of the present invention.

EXAMPLES

As revealed by the examples provided hereunder, the peptides, object of the present invention, bind the CXCR4 receptor and show both an antagonist and agonist activity on the activation of the receptor in various in vitro biological assays such as:

a) cytofluorimetric evaluation of the release of Ca$^{2+}$ following stimulation with SDF-1α;
b) modulation of the cell migratory capacity in the presence or absence of the specific ligand SDF-1α;
c) modulation of the activation of ERK-1,2.

As previously indicated, CXCR4 receptors are hyper-expressed in different tumoral pathologies. One of the functional responses to the activation of the CXCR4 receptor in relation to the relative metastatic capacity is the induction of migration. Some of the peptides of the invention have shown an antagonist action, with respect to the induction to migration induced by the ligand, almost comparable to the best characterized inhibitor AMD3100

The study carried out in vivo relating to the melanoma lung metastasis assay showed a significantly reduced number of lung metastases in the groups of mice treated with the peptides, object of the invention. Consequently the peptides of the invention, suitably selected, can be advantageously used as antitumoral agents or for the diagnosis of neoplasias.

Cell Lines

For all the subsequent in vitro examples, two cell lines were used: CCFR-CEM and PES 43; the first is a leukaemia T CD4+ cell line with a high expression of the CXCR4 receptor, grown in a RPMI 1640 culture medium enriched with 10% of Fetal Bovine Serum (FBS) inactivated with heat and 1% of L-Glutamine; the second is a cell line deriving from melanoma lung metastasis called PES43 with a high expression of the CXCR4 receptor, grown in Iscove's Modified Dulbecco's Medium (IMDM) supplemented with 10% of Fetal Bovine Serum (FBS) inactivated with heat and 1% of Penicillin-Streptomycin.

Peptides Synthesis

In the present invention, the peptides were chemically synthesized using the solid phase procedure. This technique is based on the use of a solid carrier suitably functionalized on which the complete development of the peptide chain takes place. The technique consists in binding the C-terminal amino acid of a peptide to be synthesized to an insoluble polymer and in synthesizing the peptide step-by-step in a C→N terminal direction adding the amino acid residue envisaged at each step.

When the synthesis in solid phase has been completed, the peptide is removed from the resin by appropriate treatment.

The most significant advantage of this procedure is that the purification can be effected after each synthesis cycle by simply washing the resin with a suitable solvent.

From a chemical point of view, the formation of a peptide bond comprises a condensation reaction between the free amine function of an amino acid and the free carboxyl function of a second amino acid. The formation reaction of an amide bond envisages activation of the carboxyl group. At the same time, in order to avoid side-reactions which would lead to low or zero yields, the amino acid to be bound has the α-amine function "temporarily" protected. Furthermore, the possible functional groups present on the side chains are also protected to prevent them from interfering in the condensation reaction. The side-chain groups must be stable under the deprotection conditions of the α-amine function, but easily removable in the final detachment process of the peptide from the resin.

After binding the first amino acid to the resin by means of the COOH group, each synthesis cycle is effected by means of a series of steps which can be schematized as follows:

1) removal of the protector group on the $NH_2$ of the last amino acid residue inserted in the peptide sequence;
2) accurate washing of the resin;
3) activation of the COOH of the amino acid to be reacted;
4) condensation reaction;
5) accurate washing of the resin.

The synthesis strategy which is usually performed is the so-called Fmoc, i.e. which uses as protector group for the α-amine function, the 9-fluorenylmethoxycarbonyl group (Fmoc) which can be quantitatively removed by treatment with piperidine. This strategy envisages the use of protector groups on the side-chain of amino acids which can be removed, on the contrary, under acid conditions. For the detachment from the resin and deprotection of the side-chains, a mixture of trifluoroacetic acid (TFA) and scavengers is in fact used. These reagents "block" the highly reactive species, generally carbo-cations, which are formed during the deprotection of the side-chains of the amino acid residues.

Formulae of the Cyclic Peptides of the Invention

The following Schemes 1-4 represent the general formulae of the monomeric and dimeric peptides according to the invention and the relative coding used in the text (see Tables 2-6 for the meaning and codes of the various groups).

Scheme 1: Monomers $$Nt\text{-}Ns\text{-}Nc\text{-}X_1\text{-}X_2\text{-}X_3Cc\text{-}Cs\text{-}Ct$$

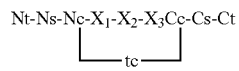

Coding: $Nt\text{-}Ns\text{-}tc: [Nc\text{-}X_1X_2X_3\text{-}Cc]\text{-}Cs\text{-}Ct$ Scheme 2: Tail-head dimers (or head-tail, through per-mutation of the subscripts 1 and 2):

$$Nt_1\text{-}Ns_1\text{-}Nc_1\text{-}X_{11}\text{-}X_{12}\text{-}X_{13}\text{-}Cc_1\text{-}Cs_1\text{-}Lnk\text{-}Ns_2\text{-}Nc_2\text{-}X_{21}\text{-}X_{22}\text{-}X_{23}\text{-}Cc_2\text{-}Cs_2\text{-}Ct_2$$

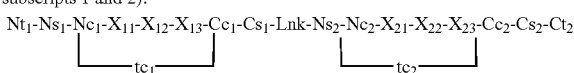

-continued
Coding: Lnk: $\{Nt_1\text{-}Ns_1\text{-}tc_1: [Nc_1\text{-}X_{11}X_{12}X_{13}\text{-}Cc_1]\text{-}Cs_1\text{-}*\}\{*\text{-}Ns_2\text{-}tc_2: [Nc_2\text{-}X_{21}X_{22}X_{23}\text{-}Cc_2]\text{-}Cs_2\text{-}Ct_2\}$ Scheme 3: Tail-tail dimers

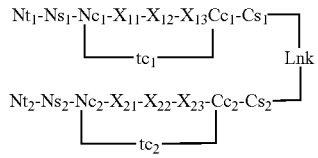

Coding: Lnk: $\{Nt_1\text{-}Ns_1\text{-}tc_1: [Nc_1\text{-}X_{11}X_{12}X_{13}\text{-}Cc_1]\text{-}Cs_1\text{-}*\}\{Nt_2\text{-}Ns_2\text{-}tc_2: [Nc_2\text{-}X_{21}X_{22}X_{23}\text{-}Cc_2]\text{-}Cs_2\text{-}*\}$ Scheme 4: Head-head dimers

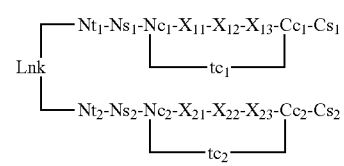

Coding: Lnk:$\{*\text{ }Ns_1\text{-}tc_1: [Nc_1\text{-}X_{11}X_{12}X_{13}\text{-}Cc_1]\text{-}Cs_1\text{-}Ct_1\}\{*\text{-}Ns_2\text{-}tc_2: [Nc_2\text{-}X_{21}X_{22}X_{23}\text{-}Cc_2]\text{-}Cs_2\text{-}Ct_2\}$ The types of central tripeptide $X_1X_2X_3$ (or $X_{11}X_{12}X_{13}$ or $X_{21}\text{-}X_{22}\text{-}X_{23}$) admissible for the peptides according to Schemes 1-4 are $Ar_1\text{-}Ar_2\text{-}B$ e $B\text{-}Ar_2\text{-}Ar_1$.

$Ar_1$ and $Ar_2$ represent aromatic amino acid residues encoded or not encoded (including peptidomimetic residues), B represents basic amino acid residues encoded or not encoded (including peptidomimetic residues). For all these residues, IUPAC-IUB one-letter codes [31] are used in the text and claims for encoded amino acids, and specific abbreviations, defined therein for the other residues.

The stereochemistry of Cα is not explicitly specified in these general formulae, which include all possible L or D chirality combinations, whereas when specific examples of peptides are described in the text or claims, the convention is adopted of using the capital letter for one-letter codes in the encoded residues or for the first letter of the abbreviation of the non-encoded residues in the case of L chiral centres, and the corresponding small letters for D chiral centres:

Table 1 below indicates the possible N-terminal (Nt) groups of peptides according to Schemes 1-4 (the empty Nt space corresponds to the omission of the corresponding code in the coding of the name of the peptide):

TABLE 1

| Name of group | Chemical formula of group | Nt code |
|---|---|---|
| None (free ammonium) | —$H^+$ | |
| Acetyl | $CH_3CO$— | Ac— |
| Formyl | HCO— | Fo- |
| tert-Butoxycarbonyl (t-Boc) | $(CH_3)_3COCO$— | tBoc- |

Table 2 indicates the possible C-terminal (Ct) groups of peptides according to Schemes 1-4 (the empty Ct space corresponds to the omission of the corresponding code in the coding of the name of the peptide):

TABLE 2

| Name of group | Chemical formula of group | Nt code |
|---|---|---|
| None (free carboxylate) | —O⁻ | |
| Primary Amide | —NH$_2$ | -Nam |
| N-methylamide | —NHCH$_3$ | —NMe |
| Methylester | —OCH$_3$ | —OMe |

Various cyclization modes are possible (tc, tc1, tc2) of the peptides according to Schemes 1-4, involving the amino acid residues Nc and Cc, which will be indicated by the corresponding IUPAC-IUB one-letter code [23] for the encoded residues, and by suitable abbreviations for non-encoded residues. For the latter, we are citing, for non-limiting illustrative purposes, some of the most widely-used abbreviations: β-Ala=β-alanin, Dap=α,β-diaminopropionic acid, Dab=α,γ-diaminobutyric acid, Orn=ornithine. For the absolute stereochemistry of the Nc and Cc residues, the same convention described above will be used.

Table 3 below illustrates these different cyclization modes.

TABLE 3

| Description of bond | tc code |
|---|---|
| Disulfide bridge between cysteine side-chains | css |
| Peptide bond via main chain (backbone-backbone) | abb |
| Backbone-sidechain amide bond | abs |
| Sidechain-backbone amide bond | asb |
| Sidechain-sidechain amide bond | asc |
| Backbone-sidechain ester bond | ebs |
| Sidechain-backbone ester bond | esb |
| Sidechain-sidechain ester bond | esc |

Table 4 shows the possible sequences of the peptides at the N- (Ns) and C-terminal (Cs) ends of the cyclic peptide according to Schemes 1-4. The notation adopted, and the considerations on the stereochemistry are the same as those indicated above. "x" represents any residue, and in round brackets the ends are indicated, at which the peptide can be adopted:

TABLE 4

| No peptide (Ns, Cs) |
|---|
| B-x- (Ns) |
| B-x-x- (Ns) |
| B-x-x-x- (Ns) |
| -x-B (Cs) |
| -x-x-B (Cs) |
| -x-x-x-B (Cs) |

Table 5 indicates the possible covalent linkers (Lnk) for the dimerization of the peptides according to Schemes 2-4.

TABLE 5

| Name of linker | Chemical formula of linker | Nt code |
|---|---|---|
| None (direct bond) | | 0 |
| 1,6-diaminohexane or Hexamethylenediamine | —HN—(CH$_2$)$_6$—NH— | N6 |
| Polyethyleneglycol (PEG) 600 | —O—(C$_2$H$_4$O)$_n$— | PEG600 |
| PEG 300-aminomalonyl-PEG 300 | —O—(C$_2$H$_4$O)$_m$—COCH(NH$_2$)CO—O—(C$_2$H$_4$O)$_n$— | 2P300AM |

EXAMPLES

Monomer with Acetyl N-terminal group, N-terminal sequence Lys-Gly, closing of the cycle between a Dap residue and a Glu residue via sidechain-sidechain amide bond, central tripeptide Phe-His-Arg, C-terminal sequence null and primary amide C-terminal group: Ac-KG-asc:[Dap-FHR-E]-Nam (SEQ ID NO:12)

Monomer corresponding to the first example, but with out protector group at the C-terminal (free carboxylate): Ac-KG-asc:[Dap-FHR-E] (SEQ ID NO:13)

Dimer formed by the same monomer of the second example, and by a peptide similar to the monomer of the second example except for the central tripeptide, having the sequence Phe-Tyr-Lys, tail-tail dimerized via 1,6-hexylene-diamine:
N6:{Ac-KG-asc:[Dap-FHR-E]-*} {Ac-KG-asc:[Dap-FYK-E]-*}

Example 1

In Vitro Assays: Cytofluorimetric Determination of the Release of Ca$^{2+}$

The determination of the release of intracellular Calcium was effected in CCFR-CEM cells. The cells (500,000 cells) were washed with PBS, resuspended in 1 ml of Loading Buffer (PBS 1×, 1 mM CaCl$_2$, 1 mM MgCl$_2$, 1% FBS inactivated with heat) at 37° C., and incubated with 4 ul of the calcium tracer FLUO3-AM (1 mg/ml; Sigma) and 4 ul of Pluronic Acid F-127 (1 mg/ml in 2% of DMSO; Invitrogen) in the dark for 30' at 37° C. under stirring. In order to remove the excess FLUO3-AM, 3 ml of Loading Buffer are added, this is followed by a centrifugation for 5' at 1,000-1,200 rpm. The pellet thus obtained is resuspended in 1 ml of Loading Buffer. The specific inhibitor of CXCR4 AMD3100 and/or the peptide tested is added at a concentration of 10 uM; incubation in the dark (15 minutes at room temperature) followed by cytofluorimetric analysis:

determination of the calcium release in the presence of a specific ionophore (ionomycin 1 mg/ml) in cells identified as vital (no accumulation of propidium iodide) represents the maximum calcium release.

determination of the calcium release in the presence of a specific ligand for the CXCR4 receptor (SDF-1α) in cells identified as vital, is considered the positive control.

determination of the calcium release in the presence of a specific ligand for the CXCR4 receptor (SDF-1α) and AMD3100 (10 uM) in cells identified as vital, is considered the negative control.

Through cytofluorimetric evaluation of the release of Ca$^{2+}$ the authors demonstrated that some of these peptides exert an antagonist activity on the activation of the receptor following stimulation with SDF-1α. In particular, the best results were obtained with the use of the peptides Ac-css:[C-WHR-C]-Nam, css:[C-FFR-C], css:[C-FFR-C]-Nam, RA-css:[C-RYW-C]. As shown in FIG. 1, the addition of the above peptides reduced Calcium release. In particular, Ac-css:[C-WHR-C]-Nam by 40.7%, css:[C-FFR-C] by 53.3%, css:[C-FFR-C]-Nam by 59.9% and RA-css:[C-RYW-C] by 56%. Furthermore, peptides were also identified by means of this test, with a possible agonist function such as, for example, Ac-css:[C-WHR-C], Ac-css:[C-FFR-C], Ac-css:[C-WYR-C] and css:[C-FFR-C]-AR which show an increase in the receptor activity in the release of the calcium ion. This increase is equal to 104% for css:[C-FFR-C]-AR, 106% for Ac-css:[C-FFR-C], 113.7% for Ac-css:[C-WYR-C] and 121% for Ac-css:[C-WHR-C].

The activity of the peptides was compared with that of AMD3100 used as inhibitor of $Ca^{2+}$ release. Consequently: The peptides: Ac-css:[C-WHR-C]-Nam (40%), css:[C-FFR-C] (53.3%), css:[C-FFR-C]-Nam (59.9%) and RA-css:[C-RYW-C] (56%), inhibit the $Ca^{2+}$ release induced by the activation of the receptor on the part of SDF-1α;
AMD3100 (10 uM) inhibits the release of the $Ca^{2+}$ ion induced by SDF-1α by 70%.

Example 2

In vitro Assays: Quantitative Determination of the Fluorescence

The bond of the peptides to the CXCR4 receptor was indirectly tested by means of flow cytofluorimetry, with the use of a phycoerythrinate antibody anti-CXCR4 (R&D, Inc.).

In order to obtain a qualitative measurement of the ratio of bond between peptides and CXCR4, the cells were incubated with the peptide for 30' and then incubated again in the presence of the antibody anti-CXCR4. In order to verify the number of receptor molecules available for the antibody anti-CXCR4, a test was used, which allows the number of fluorescent antibodies bound to the cell to be quantified by comparing the fluorescence value obtained with the known value of fluorescent spheres conjugated with phycoerythrin (PELe cells CCRF-CEM (500,000 cells/ml), they are grown in RPMI 1640+1% Glutamine, treated with AMD3100 or peptide (10 uM) and incubated at 37° C. for 30'. A washing is effected with 2 ml of PBS 1× and another washing with 2 ml of PBS+0.5% BSA, centrifuging for 5' at 1,000-1,200 rpm. 5 ul of monoclonal antibody anti-CXCR4 are added to the pellet together with a new dose of AMD3100 or peptides and the pellet is incubated for 30'-45' in ice, in the dark. A new washing is effected with PBS+0.5% BSA, resuspending the cells in 500 ul of PBS; this is followed by cytofluorimetric analysis. For the determination of the binding of the peptides to CXCR4, a known fluorescence sample was used as standard (PE Fluorescence quantification Kit, BD Inc.).

The results obtained are indicated in FIG. 2, from which the binding affinity of the peptides css:[C-WHR-C], RA-css:[C-RYW-C], RA-css:[C-RFF-C] and RA-css:[C-RHW-C] can be deduced, for the CXCR4 receptor. In particular, the quantity of normalized fluorescence registered, with the various peptides is: css:[C-WHR-C] 45%; RA-css:[C-RYW-C] 22%; RA-css:[C-RFF-C] 21%; RA-css:[C-RHW-C] 17%.

Consequently the use of the peptides css:[C-WHR-C] (45%), RA-css:[C-RFF-C] (21%), RA-css:[C-RHW-C] (17%) and RA-css:[C-RYW-C] (21%) considerably reduced the number of antibodies bound per cell, and therefore led to a decrease in the fluorescence per cell; this shows that these peptides are capable of binding CXCR4 thus displacing the antibody anti-CXCR4.

Example 3

In vitro Assays: Modulation of the Cell Migratory Capacity in the Presence or Absence of the Specific Ligand SDF-1α

Migration induction is one of the functional responses to the activation of the CXCR4 receptor in relation to the relative metastatic capacity. The evaluation of the activity of the peptides in receptor interaction was evaluated through the migration test. A human melanoma cell line, PES43, was used, previously characterized by expression of CXCR4 and migratory capacity in response to increasing concentrations of SDF-1α.

The migration was tested in specific transwell plates having 24 wells using baskets (Corning Inc., Corning, N.Y.) with membranes having pores of 8 μm. The membranes were coated with collagen (human collagen of the type I/III) and fibronectin (20 μg/ml each) The human melanoma cells PES43 were sown in the upper basket ($2.5 \times 10^5$ cells/well) in IMDM culture medium containing 1% of BSA (migration medium), and 20 ng/ml of SDF-1α were added to the lower basket. The experiment was carried out at least three times. After 16 hours of incubation, the cells in the upper surface of the filter were removed using a padded rod. The migration of the cells towards the serum-free migration medium was compared with the migration towards 20 ng/ml of SDF-1α. The cells were counted in 10 different fields with a magnification of 40×. The migration index was defined as the ratio between the migration of the cells of the experimental group divided by that of the control group. The positive control of the experiment consisted of the migration of the cells towards the serum.

Through the migration test, the interference activity with the migration on the part of the following peptides was demonstrated: css:[C-WHR-C], css:[C-WYR-C]-AR, RA-css:[C-RFF-C], RA-css:[C-RHW-C], RA-css:[C-RYW-C], abb:[β-Ala-WHR-β-Ala], css:[C-WWR-C].

These peptides showed an antagonist action with respect to migration induction induced by the ligand almost comparable with the most highly characterized inhibitor AMD3100. The activity of the peptides inhibiting migration induced by the ligand is compared with the inhibition mediated by AMD3100. In particular, the reductions in migration normalized for the control are equal to: css:[C-WHR-C] 80%; css:[C-WYR-C]-AR 40%; RA-css:[C-RFF-C] 20%; RA-css:[C-RHW-C] 75%; RA-css:[C-RYW-C] 20%; abb:[β-Ala-WHR-β-Ala] 45%; css:[C-WWR-C] 37%.

Furthermore, it was revealed that the peptides css:[C-FFR-C]-Nam and css:[C-WHR-C]-AR cause an increase in the cell mobility in response to SDF-1α, and therefore have an additional action with respect to SDF-1α equal to 190% for css:[C-FFR-C]-Nam and 170% for css:[C-WHR-C]-AR, i.e. equal to almost the double of that of the non-treated basal (FIG. 3).

Example 4

In vitro Assays: Modulation of the Activation of ERK-1,2

The activation of CXCR4 induces the transduction path of MAPK through the phosphorylation of ERK 1,2. For this reason, the modulation of the induction of P-ERK was evaluated in relation to treatment with SDF-1α (100 ng/ml), peptides (10 uM) and AMD3100 (1 uM).

In order to demonstrate that SDF-1α activates a cascade of signals downstream, we examined the activation of ERK 1/2 in PES43 by means of Immunoblotting with antibodies which recognize the phosphorylated form (and therefore active) of these two kinases. The cells were deprived of serum for 24 hours and then stimulated with SDF-1α.

The human melanoma cells, PES43, grown on 100 mm plates, were treated with SDF-1α, for 2-5-7-10 minutes. The cells were then mechanically detached, lysed in a specific buffer to which protease inhibitors and phosphatase inhibitors were added (120 mM NaCl, 40 mM Hepes, 5 mM $MgCl_2$, 1 mM EGTA, 0.5 mM EDTA, 0.6% Triton, 10% glycerol, 10 mM aprotinin, 1 mM Na$_3$VO$_4$, 1 mM NaF). The cell lysates thus obtained (50 µg of total proteins) were first denatured with Laemmli 4× and then separated with SDS-PAGE on gel at 10% in the presence of a running buffer (Tris Base, Glycine, SDS); the proteins were subsequently transferred onto a nitrocellulose membrane in incubated with primary antibodies specific for the following proteins: phospho-ERK 1/2, total ERK. The filters were then washed with 0.01M T-TBS and incubated with the relative secondary antibodies. The visualization of the immunocomplexes was effected using ECL.

Through this experiment, we observed that SDF-1α is capable of inducing the phosphorylation of ERK 1, 2 at 2 and 5 minutes.

The ligand SDF-1α activates the phosphorylation of ERK and this phosphorylation is inhibited by both AMD3100 (1 uM) and by the peptides css:[C-WHR-C] (10 uM), css:[C-FFR-C] (10 uM), css:[C-FFR-C]-Nam (10 uM), css:[C-WYR-C]-AR (10 uM), RA-css:[C-RFF-C] (10 uM), RA-css: [C-RHW-C] (10 uM), abb:[β-Ala-WHR-β-Ala] (10 uM). A discrete agonist capacity in the presence of SDF-1α was also observed, on the part of the peptides Ac-css:[C-WHR-C] (10 uM), Ac-css:[C-WYR-C] (10 uM), Ac-css:[C-WYR-C]-Nam (10 uM), css:[C-WHR-C]-Nam (10 uM), css:[C-WYR-C]-Nam (10 uM), css:[C-FFR-C]-AR (10 uM) and css:[C-WHR-C]-AR (10 uM).

In order to better analyze a possible agonist action on the part of the above peptides, their activity without SDF-1α was evaluated. From this analysis, it can be seen that the induction of p-ERK is equal to 300% (compared with SDF-1α) following treatment with the peptides Ac-css:[C-WYR-C] (10 uM), Ac-css:[C-WYR-C]-Nam (10 uM) and css:[C-WHR-C]-AR (10 uM).

In conclusion, from an evaluation of p-ERK, the behaviour of the following peptides: css:[C-WHR-C]; css:[C-FFR-C]; css:[C-FFR-C]-Nam; css:[C-WYR-C]-AR; RA-css:[C-RFF-C]; RA-css:[C-RHW-C]; abb:[β-Ala-WHR-β-Ala] as antagonists and of the following peptides: Ac-css:[C-WYR-C], Ac-css:[C-WYR-C]-Nam, css:[C-WHR-C]-AR as agonists, can be deduced (see FIG. 4).

Example 5

In vivo Studies: Melanoma Lung Metastasis Assay

The in vivo study was carried out on 25 female mice C57/B, between the sixth and eighth week of life and with a weight of about 18 g, acquired from Charles-River Italia (Milan, Italy). The mice were kept under specific conditions according to the protocols approved by the "G. Pascale" Foundation in accordance with the guidelines for the treatment and use of animals, of the Italian Ministry of Health. The animals were acclimatized for a week, before beginning the injections with neoplastic cells.

The mice were divided into 5 groups, of 5 mice for each group, depending on the treatment:
GROUP A: treatment with 100 µL PBS
GROUP B: treatment with 1.25 mg/Kg AMD 3100 in 100 µL of PBS
GROUP C: treatment with 2 mg/Kg RA-css:[C-RHW-C] in 100 µL of PBS.
GROUP D: treatment with 2 mg/Kg RA-css:[C-RFF-C] in 100 µL of PBS.
GROUP E: treatment with 2 mg/Kg css:[C-WHR-C] in 100 µL of PBS.

B16-CXCR4 cells (500,000 cells/mouse) were separated by means of trypsin and washed twice in PBS; they were then pre-treated with
GROUP A: no treatment
GROUP B: 10 µM AMD3100
GROUP C: 10 µM RA-css:[C-RHW-C]
GROUP D: 10 µM RA-css:[C-RFF-C]
GROUP E: 10 µM css:[C-WHR-C].

The pre-treatment was effected for 30 minutes at 37° C.

5×10$^5$ B16-CXCR4, resuspended in 100 µL of PBS were then inoculated into the caudal vein. In the same day (T0) the treatment was initiated systemically by a daily intraperitoneal injection, for 5 days a week, for two weeks.

In particular:
GROUP A: treatment with 100 µL PBS
GROUP B: treatment with 1.25 mg/Kg AMD 3100 in 100 µL of PBS
GROUP C: treatment with 2 mg/Kg RA-css:[C-RHW-C] in 100 µL of PBS.
GROUP D: treatment with 2 mg/Kg RA-css:[C-RFF-C] in 100 µL of PBS.
GROUP E: treatment with 2 mg/Kg css:[C-WHR-C] in 100 µL of PBS.

On the 21$^{st}$ day of injection, the animals were sacrificed and the organs explanted (lungs, liver and spleen), two operators distinctly provided for the examination of the same and setting up of the histological preparations. The only organs in which metastases were found were the lungs, the metastatic lesions present therein were then counted. Macroscopic and microscopic analysis showed a significantly reduced number of lung metastases in the groups of mice treated with the peptides RA-css:[C-RFF-C], RA-css:[C-RHW-C], css:[C-WHR-C] (see FIG. 5).

BIBLIOGRAPHY

[1] Scala S, Giuliano P, Ascierto P A, Ierano C, Franco R, Napolitano M, Ottaiano A et al (2006) *Clin Cancer Res* 12: 2427-2433.
[2] Scala S, Ottaiano A, Ascierto P A, Cavalli M, Simeone E, Giuliano P, Napolitano M, Franco R, Botti G, Castello G. (2005). *Clin Cancer Res* 11: 1835-184.
[3] Ottaiano A, Franco R, Aiello Talamanca A, Liguori G, Tatangelo F, Delrio P, Nasti G, Barletta E, Facchini G, and Scala S. Clin Cancer Res. 2006 May 1; 12(9):2795-803.
[4] Hendrix, C W, Flexner, C1, Mc Farland, R T, Giandomenico, C, Fuchs, E J, Redpath, E, Bridger, G2 and Henson, G W. ANTIMICROBIAL AGENTS AND CHEMOTHERAPY, June 2000, p. 1667-1673 Vol. 44, No. 6.
[5] De Clerq E. Biochem Pharmacol. 2009 Jun. 1; 77(11): 1655-64. Epub 2008 Dec. 31. Review.
[6] DiPersio J F, Micallef I N, Stiff P J, Bolwell B J, Maziarz R T, Jacobsen E, Nademanee A, McCarty J, Bridger G, Calandra G; 3101 Investigators. J. Clin. Oncol. 2009 Oct. 1; 27(28):4767-73.
[7] Zisa D, Shabbir A, Mastri M, Suzuki G, Lee T. Am. J. Physiol. Regul. Integr. Comp. Physiol. 2009 November; 297(5):R1503-15.
[8] Bonaros N, Sondermejer H, Schuster M, Rauf R, Wang S F, Seki T, Skerrett D, Itescu S, Kocher A A. J. Thorac. Cardiovasc. Surg. 2008 October; 136(4):1044-53.
[9] Yuan Y, Kan H, Fang Q, Chen F, Finkel M S. Cardiovasc Toxicol. 2008 December; 8(4):173-80.
[10] Athanassopoulos P, Vaessen L M, Balk A H, Weimar W, Sharma H S, Bogers A J. Cell. Biochem. Biophys. 2006; 44(1):83-101.

[11] Opatz J, Kliry P, Schiwy N, Järve A, Estrada V, Brazda N, Bosse F, Müller H W Mol Cell Neurosci. 2009 February; 40(2):293-300. Epub 2008 Nov. 24.
[12] Giri B, Dixit V D, Ghosh M C, Collins G D, Khan I U, Madara K, Weeraratna A T, Taub D D. Eur. J. Immunol. 2007 August; 37(8):2104-16.
[13] Corti S, Locatelli F, Papadimitriou D, Del Bo R, Nizzardo M, Nardini M, Donadoni C, Salani S, Fortunato F, Strazzer S, Bresolin N, Comi G P. Brain. 2007 May; 130(Pt 5):1289-305.
[14] Fulton A M. Curr Oncol Rep. 2009 March; 11(2):125-31.
[15] Wong D, Korz W. Clin Cancer Res. 2008 Dec. 15; 14(24):7975-80. Review.
[16] Fauchere, J., *Adv. Drug Res.* 15: 29 (1986);
[17] Veber and Freidinger, TINS 392 (1985);
[18] Evans et al., *J. Med. Chem.* 30: 1229 (1987)
[19] Spatola, A. F. in CHEMISTRY AND BIOCHEMISTRY OF AMINO ACIDS, PEPTIDES, AND PROTEINS 267 (B. Weinstein, edz. 1983)
[20] Spatola, A. F., *Vega Data* Vol. 1, Issue 3, "Peptide Backbone Modifications" (March 1983)
[21] Morley, J. S., *Trends Pharm Sci.*, pp. 463-468 (1980)
[22] Hudson, D. et al., *Int. J. Pept. Prot. Res.* 14: 177-185 (1979) (—$CH_2NH$—, $CH_2CH_2$—)
[23] Spatola, A. F. et al., *Life Sci.* 38: 1243-1249 (1986) (—$CH_2$—S)
[24] Hann, M., *J. Chem. Soc. Perkin Trans. I* 307-314 (1982) (—CH—CH—, cis and trans)
[25] Alnquist, R. G. et al., *J. Med. Chem.* (1980) 23: 1392-1398 (—$COCH_2$—)
[26] Jennings-White, C. et al., *Tetrahedron Lett.* 23: 2533 (1982) (—$COCH_2$—)
[27] EP 45665 (1982) CA: 97: 39405 (1982) (—CH(OH)$CH_2$—)
[28] Holladay, M. W. et al., *Tetrahedron Lett.* 24: 4401-4404 (1983) (—C(OH)$CH_2$—)
[29] Hruby, V. J., *Life Sci.* 31: 189-199 (1982)(—$CH_2$—S—)
[30] REMINGTON'S PHARMACEUTICAL SCIENCES (Mack Publishing Co., Easton, 19a ed. 1995.
[31] Arch. Biochem. Biophys. 115: 1-12.

The invention claimed is:

1. Cyclic monomeric peptides containing up to eight amino acids characterised in that they exert an agonist or antagonist action on the CXCR4 receptor and that they have the following general formula (I):

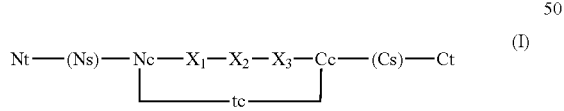

wherein:
the N- terminal group Nt of the peptide is selected between free amine and acetyl (Ac);
the C terminal group Ct of the peptide is selected between free carboxylate, and primary amide (Nam);
the N terminal sequence (Ns) optionally present has a formula selected between B-x-; and
B-x-x;
the C terminal sequence (Cs) optionally present is -x-B;
wherein B represents an encoded basic amino acid residue selected from lysine (K) and arginine (R) and wherein x represents an encoded amino acid residue selected from glycine (G), alanine (A) and proline (P); wherein said sequences (Ns) and (Cs) may be present with mutual exclusion or both be absent;
both amino acid residues Nc and Cc, are cysteine (C) and are both present;
the bond tc that involves the amino acid residues Nc and Cc in the ring formation is—a disulphide bridge between cysteine side chains (css);
the central sequence $X_1$-$X_2$-$X_3$ is selected from $Ar_1$-$Ar_2$-R and R-$Ar_2$-$Ar_1$, wherein R is arginine, and $Ar_1$-$Ar_2$ are encoded aromatic residues selected from phenylalanine (F), tryptophan (W), tyrosine (Y) and histidine (H);
or pharmacologically acceptable salts thereof.

2. Peptides according to claim 1, wherein the N terminal sequence Ns is: a) absent; or b) a dipeptide RA or c) a tripeptide selected from RPA or KAP.

3. Peptides according to claim 1, wherein the C terminal sequence Cs is: a) absent; or b) a dipeptide AR.

4. Peptides according to claim 1, wherein the central sequence $X_1$-$X_2$-$X_3$ is selected between RHW, RFF, WHR, FHR, FYR, RYF, FFR, WYR, RYW, WFR, RFW.

5. A peptide wherein said peptide has a modulatory activity on a CXCR4 receptor and where said peptide is selected from the group consisting of:

(SEQ ID NO: 1)
Ac-C-W-H-R-C-Nam
    |_css_|
(SEQ ID NO: 2)
C-F-F-R-C
 |_css_|
(SEQ ID NO: 3)
C-W-H-R-C
 |_css_|
(SEQ ID NO: 4)
R-A-C-R-Y-W-C
   |_css__|
(SEQ ID NO: 5)
C-F-F-R-C-Nam
 |_css_|
(SEQ ID NO: 6)
C-W-Y-R-C-A-R
 |_css_|
(SEQ ID NO: 7)
R-A-C-R-F-F-C
   |_css__|
(SEQ ID NO: 8)
R-A-C-R-H-W-C
   |_css__|
(SEQ ID NO: 9)
βAla-W-H-R-βAla
   |__abb__|
(SEQ ID NO: 10)
C-W-H-R-C-A-R
 |_css_|
(SEQ ID NO: 11)
C-W-W-R-C
 |_css_|
(SEQ ID NO: 12)
Ac-K-G-Dap-F-H-R-E
         |___asc___|
(SEQ ID NO: 13)
Ac-K-G-Dap-F-H-R-E-Nam
         |__asc__|

(SEQ ID NO: 14)
Ac-C-W-H-R-C
    |_css_|
(SEQ ID NO: 15)
Ac-C-F-F-R-C
    |_css_|
(SEQ ID NO: 16)
C-W-H-R-C-A-R
 |_css_|
(SEQ ID NO: 17)
Ac-C-W-Y-R-C
    |_css_|
(SEQ ID NO: 18)
C-F-F-R-C-A-R
 |_css_|
(SEQ ID NO: 19)
Ac-C-W-Y-R-C-Nam
    |_css_|
(SEQ ID NO: 20)
C-W-H-R-C-Nam
 |_css_|
(SEQ ID NO: 21)
C-W-Y-R-C-Nam
 |_css_|
(SEQ ID NO: 22)
C-R-H-W-C
 |_css_|
(SEQ ID NO: 23)
R-P-A-C-R-F-F-C
     |__css__|
(SEQ ID NO: 24)
K-A-P-C-R-F-F-C.
       |_css_| where Ac is acetyl, C is cysteine, W is tryptophan, H is histidine, R is arginine, Nam is $NH_2$, F is phenylalanine, Y is tyrosine, A is alanine and css is a disulphide bridge between cysteine side chains.

\* \* \* \* \*